US012396970B2

(12) United States Patent
Kashfian et al.

(10) Patent No.: US 12,396,970 B2
(45) Date of Patent: Aug. 26, 2025

(54) ANTI-ARRHYTHMIC COMPOSITIONS AND METHODS

(71) Applicant: AltaThera Pharmaceuticals LLC, Chicago, IL (US)

(72) Inventors: Brandon Ira Kashfian, Chicago, IL (US); Jodi Devlin, Chicago, IL (US)

(73) Assignee: AltaThera Pharmaceuticals LLC, Chicago, IL (US)

( * ) Notice: Subject to any disclaimer, the term of this patent is extended or adjusted under 35 U.S.C. 154(b) by 400 days.

(21) Appl. No.: 17/892,301

(22) Filed: Aug. 22, 2022

(65) Prior Publication Data
US 2023/0172883 A1 Jun. 8, 2023

Related U.S. Application Data

(63) Continuation-in-part of application No. 17/566,840, filed on Dec. 31, 2021, now Pat. No. 11,610,660.

(60) Provisional application No. 63/345,068, filed on May 24, 2022, provisional application No. 63/344,154, filed on May 20, 2022, provisional application No. 63/340,581, filed on May 11, 2022, provisional application No. 63/334,267, filed on Apr. 25, 2022, provisional application No. 63/331,905, filed on Apr. 18, 2022, provisional application No. 63/276,947, filed on Nov. 8, 2021, provisional application No. 63/235,500, filed on Aug. 20, 2021.

(51) Int. Cl.
| A61K 31/18 | (2006.01) |
| A61P 9/06 | (2006.01) |
| A61K 9/00 | (2006.01) |

(52) U.S. Cl.
CPC .............. *A61K 31/18* (2013.01); *A61P 9/06* (2018.01); *A61K 9/0019* (2013.01)

(58) Field of Classification Search
None
See application file for complete search history.

(56) References Cited

U.S. PATENT DOCUMENTS

| 6,043,273 A | 3/2000 | Duhaylongsod |
| 6,060,454 A | 5/2000 | Duhaylongsod |
| 6,101,412 A | 8/2000 | Duhaylongsod |
| 6,124,363 A | 9/2000 | Appleby et al. |
| 6,136,327 A | 10/2000 | Gupta et al. |
| 6,281,246 B2 | 8/2001 | Sankaranarayanan |
| 6,369,114 B1 | 4/2002 | Weil et al. |
| 6,482,811 B1 | 11/2002 | Bacaner et al. |
| 6,491,039 B1 | 12/2002 | Dobak, III |
| 6,500,459 B1 | 12/2002 | Chhabra et al. |
| 6,544,981 B2 | 4/2003 | Stein et al. |
| 6,627,223 B2 | 9/2003 | Percel et al. |
| 6,632,217 B2 | 10/2003 | Harper et al. |
| 6,645,524 B2 | 11/2003 | Midha et al. |
| 6,720,001 B2 | 4/2004 | Chen et al. |
| 6,800,668 B1 | 10/2004 | Odidi et al. |
| 6,899,700 B2 | 5/2005 | Gehling et al. |
| 6,916,813 B2 | 7/2005 | Atwal et al. |
| 6,944,638 B1 | 9/2005 | Putnam |
| 7,004,171 B2 | 2/2006 | Benita et al. |
| 7,005,425 B2 | 2/2006 | Belardinelli et al. |
| 7,005,436 B2 | 2/2006 | Lloyd et al. |
| 7,022,343 B2 | 4/2006 | Philbrook et al. |
| 7,048,945 B2 | 5/2006 | Percel et al. |
| 7,090,830 B2 | 8/2006 | Hale et al. |
| 7,179,597 B2 | 2/2007 | Woosley |
| 7,289,847 B1 | 10/2007 | Gill et al. |
| 7,341,737 B2 | 3/2008 | Gehling et al. |

(Continued)

FOREIGN PATENT DOCUMENTS

| AU | 737668 B2 | 8/2001 |
| AU | 765269 B2 | 9/2003 |

(Continued)

OTHER PUBLICATIONS

Bianconi et al., publication titled "Comparison of intravenously administered dofetilide versus amiodarone in the acute termination of atrial fibrillation and flutter", (Year: 2000).*
Dailymed website: https://dailymed.nlm.nih.gov/dailymed/fda/fdaDrugXsl.cfm?setid=02438044-d6a3-49e9-a1ac-3aad21ef2c8c (Year: 1999).*
Co-Pending U.S. Appl. No. 16/103,815, Response to Feb. 6, 2019 Non-Final Office Action, filed May 6, 2019, 17 pages.

(Continued)

*Primary Examiner* — Manuel A Mendez
(74) *Attorney, Agent, or Firm* — New River Valley IP Law, P.C.; Michele L. Mayberry; Ashley M. Gates

(57) ABSTRACT

Methods of administering an anti-arrhythmic, such as dofetilide, to a patient in an amount effective for treating a cardiovascular condition are described. The drug can be administered intravenously for at least one hour. A loading dose of 0.1 to 12 μg/kg bodyweight over a duration of up to 60 minutes can be administered and/or a maintenance dose of 0.1 to 10 μg/kg/hr can be administered intravenously over a duration of at least 1 hour, optionally alternatively or in addition wherein the amount of the loading dose and/or the IV maintenance dose is in the range of about ±50% of a maintenance dofetilide dose. The cardiovascular condition can include atrial fibrillation or flutter, ventricular tachycardia, hemodynamically stable or unstable ventricular tachycardia, paroxysmal atrial fibrillation, ventricular fibrillation, paroxysmal supraventricular tachycardia, heart failure, coronary artery disease, or pulmonary artery hypertension. A patient's QT interval and/or a creatinine clearance can be measured, and the effective amount can be selected based on either or both of the QT interval or the creatinine clearance measurements.

22 Claims, No Drawings

(56) References Cited

U.S. PATENT DOCUMENTS

| | | |
|---|---|---|
| 7,371,254 B2 | 5/2008 | Dobak, III |
| 7,396,524 B2 | 7/2008 | Yan |
| 7,417,038 B1 | 8/2008 | Anker et al. |
| 7,526,335 B2 | 4/2009 | Ferek-Petric |
| 7,538,092 B2 | 5/2009 | Orlando et al. |
| 7,572,776 B2 | 8/2009 | Yu et al. |
| 7,674,820 B2 | 3/2010 | Fedida et al. |
| 7,745,665 B2 | 6/2010 | Gant et al. |
| 7,765,110 B1 | 7/2010 | Koneru |
| 7,776,844 B2 | 8/2010 | Yu et al. |
| 7,815,936 B2 | 10/2010 | Hasenzahl et al. |
| 7,829,573 B2 | 11/2010 | Curwen et al. |
| 7,846,968 B2 | 12/2010 | Chien et al. |
| 7,885,824 B1 | 2/2011 | Koneru |
| 7,885,827 B1 | 2/2011 | Koneru |
| 7,951,183 B2 | 5/2011 | Dobak, III |
| 8,106,099 B2 | 1/2012 | Brendel et al. |
| 8,236,782 B2 | 8/2012 | Mosher et al. |
| 8,263,125 B2 | 9/2012 | Vaya et al. |
| 8,268,352 B2 | 9/2012 | Vaya et al. |
| 8,313,757 B2 | 11/2012 | Lengerich |
| 8,377,994 B2 | 2/2013 | Gray et al. |
| 8,399,018 B2 | 3/2013 | Lichter et al. |
| 8,440,168 B2 | 5/2013 | Yang et al. |
| 8,465,769 B2 | 6/2013 | Petereit et al. |
| 8,466,277 B2 | 6/2013 | Orlando et al. |
| 8,575,348 B2 | 11/2013 | Rao et al. |
| 8,696,696 B2 | 4/2014 | Solem |
| 8,709,076 B1 | 4/2014 | Matheny et al. |
| 8,753,674 B2 | 6/2014 | Helson |
| 8,828,432 B2 | 9/2014 | Lengerich |
| 8,865,213 B2 | 10/2014 | Sheth et al. |
| 8,871,452 B2 | 10/2014 | Lee |
| 8,906,847 B2 | 12/2014 | Cleemann et al. |
| 8,962,574 B2 | 2/2015 | Reilly |
| 8,987,262 B2 | 3/2015 | Leaute-Labreze et al. |
| 9,011,526 B2 | 4/2015 | Matheny |
| 9,016,221 B2 | 4/2015 | Brennan et al. |
| 9,044,319 B2 | 6/2015 | Matheny |
| 9,060,969 B2 | 6/2015 | Matheny |
| 9,078,929 B2 | 7/2015 | Kuebelbeck et al. |
| 9,161,952 B2 | 10/2015 | Matheny et al. |
| 9,239,333 B2 | 1/2016 | Snider |
| 9,255,104 B2 | 2/2016 | Rao et al. |
| 9,308,084 B2 | 4/2016 | Matheny |
| 9,399,067 B2 | 7/2016 | Mosher et al. |
| 9,474,719 B2 | 10/2016 | Mullen et al. |
| 9,498,481 B2 | 11/2016 | Rao et al. |
| 9,549,912 B2 | 1/2017 | Milner et al. |
| 9,554,989 B2 | 1/2017 | Kaplan et al. |
| 9,585,851 B2 | 3/2017 | Yun et al. |
| 9,585,884 B2 | 3/2017 | Rao et al. |
| 9,597,302 B1 | 3/2017 | Yan et al. |
| 9,616,026 B2 | 4/2017 | Singh |
| 9,682,041 B2 | 6/2017 | Helson |
| 9,724,297 B2 | 8/2017 | Thomas et al. |
| 9,770,514 B2 | 9/2017 | Ghebre-Sellassie et al. |
| 9,889,148 B2 | 2/2018 | Daemmgen et al. |
| 9,995,756 B2 | 6/2018 | Saffitz et al. |
| 10,117,881 B2 | 11/2018 | Helson |
| 10,238,602 B2 | 3/2019 | Helson et al. |
| 10,258,691 B2 | 4/2019 | Helson et al. |
| 10,349,884 B2 | 7/2019 | Helson et al. |
| 10,357,458 B2 | 7/2019 | Helson |
| 10,449,193 B2 | 10/2019 | Helson et al. |
| 10,450,267 B2 | 10/2019 | Stancl |
| 10,512,620 B1 | 12/2019 | Somberg et al. |
| 10,537,588 B2 | 1/2020 | Daemmgen et al. |
| 10,603,316 B2 | 3/2020 | Xiong et al. |
| 10,617,639 B2 | 4/2020 | Helson |
| 10,793,519 B2 | 10/2020 | Somberg et al. |
| 10,799,138 B2 | 10/2020 | Ivaturi et al. |
| 10,888,524 B2 | 1/2021 | Yenkar et al. |
| 10,888,552 B2 | 1/2021 | Rothman |
| 11,286,235 B2 | 3/2022 | Somberg et al. |
| 11,344,518 B2 | 5/2022 | Somberg |
| 11,364,213 B2 | 6/2022 | Somberg |
| 11,583,216 B2 | 2/2023 | Ivaturi et al. |
| 11,610,660 B1 | 3/2023 | Devlin et al. |
| 11,696,902 B2 | 7/2023 | Somberg et al. |
| 11,957,648 B2 | 4/2024 | Somberg |
| 2007/0009564 A1 | 1/2007 | McClain et al. |
| 2007/0009654 A1 | 1/2007 | Watanabe et al. |
| 2012/0003318 A1 | 1/2012 | Schuler et al. |
| 2014/0235631 A1 | 8/2014 | Bunt et al. |
| 2014/0276404 A1 | 9/2014 | Orlowski |
| 2015/0081010 A1 | 3/2015 | Matheny |
| 2015/0210712 A1 | 7/2015 | Blumberg et al. |
| 2016/0082159 A1 | 3/2016 | Orlowski |
| 2016/0128944 A1 | 5/2016 | Chawrai et al. |
| 2016/0228379 A1 | 8/2016 | Kumar et al. |
| 2016/0271070 A1 | 9/2016 | Singh et al. |
| 2016/0271157 A1 | 9/2016 | Ahmed et al. |
| 2016/0303133 A1 | 10/2016 | Dudley et al. |
| 2016/0317388 A1 | 11/2016 | Bhargava et al. |
| 2017/0049705 A1 | 2/2017 | Mateescu et al. |
| 2017/0087105 A1 | 3/2017 | Yan et al. |
| 2017/0100387 A1 | 4/2017 | Arora et al. |
| 2017/0119627 A1 | 5/2017 | Bhargava et al. |
| 2017/0157076 A1 | 6/2017 | Yacoby-Zeevi et al. |
| 2017/0231885 A1 | 8/2017 | Cremers et al. |
| 2017/0258781 A1 | 9/2017 | Noujaim et al. |
| 2017/0296493 A1 | 10/2017 | Thomas et al. |
| 2017/0348303 A1 | 12/2017 | Bosse et al. |
| 2018/0071390 A1 | 3/2018 | Patel et al. |
| 2019/0307343 A1 | 10/2019 | Ivaturi et al. |
| 2019/0352257 A1 | 11/2019 | Somberg et al. |
| 2019/0380605 A1 | 12/2019 | Ivaturi et al. |
| 2019/0388371 A1 | 12/2019 | Somberg |
| 2019/0389888 A1 | 12/2019 | McChesney et al. |
| 2020/0085771 A1 | 3/2020 | Somberg et al. |
| 2020/0093759 A1 | 3/2020 | Somberg et al. |
| 2020/0226481 A1 | 7/2020 | Sim et al. |
| 2020/0253903 A1 | 8/2020 | Somberg |
| 2020/0338027 A1 | 10/2020 | Somberg |
| 2020/0383941 A1 | 12/2020 | Brelidze et al. |
| 2021/0076959 A1 | 3/2021 | Ivaturi et al. |
| 2021/0107867 A1 | 4/2021 | Somberg et al. |
| 2021/0283049 A1 | 9/2021 | Somberg |
| 2021/0346325 A1 | 11/2021 | Somberg |
| 2022/0142954 A1 | 5/2022 | Somberg |
| 2022/0241225 A1 | 8/2022 | Somberg |
| 2022/0339130 A1 | 10/2022 | Somberg et al. |
| 2023/0075398 A1 | 3/2023 | Devlin et al. |
| 2023/0187049 A1 | 6/2023 | Devlin et al. |
| 2023/0225664 A1 | 7/2023 | Ivaturi et al. |
| 2023/0225997 A1 | 7/2023 | Kashfian |
| 2023/0248674 A1 | 8/2023 | Kashfian |
| 2023/0255908 A1 | 8/2023 | Kashfian |
| 2023/0255909 A1 | 8/2023 | Kashfian |
| 2023/0270940 A1 | 8/2023 | Devlin et al. |
| 2023/0285273 A1 | 9/2023 | Kashfian |
| 2023/0293426 A1 | 9/2023 | Kashfian |
| 2023/0293455 A1 | 9/2023 | Somberg et al. |
| 2023/0310745 A1 | 10/2023 | Kashfian |
| 2023/0372268 A1 | 11/2023 | Kashfian |
| 2024/0156758 A1 | 5/2024 | Somberg |
| 2024/0261242 A1 | 8/2024 | Kashfian |
| 2025/0140361 A1 | 5/2025 | Kashfian et al. |
| 2025/0152529 A1 | 5/2025 | Somberg et al. |
| 2025/0152530 A1 | 5/2025 | Somberg et al. |
| 2025/0213504 A1 | 7/2025 | Kashfian et al. |

FOREIGN PATENT DOCUMENTS

| | | |
|---|---|---|
| AU | 2003233653 A1 | 12/2003 |
| AU | 2005299693 A1 | 5/2006 |
| AU | 2010231494 A1 | 11/2011 |
| AU | 2013203252 A1 | 8/2013 |
| AU | 2013381856 A1 | 7/2015 |
| AU | 2011289176 B2 | 9/2015 |
| AU | 2016266020 B2 | 10/2018 |
| AU | 2017357916 A1 | 5/2019 |
| AU | 2016313439 B2 | 10/2019 |

(56) References Cited

FOREIGN PATENT DOCUMENTS

| | | |
|---|---|---|
| AU | 2015269699 B2 | 8/2020 |
| EP | 0898964 A1 | 3/1999 |
| EP | 1027329 B1 | 2/2003 |
| EP | 1467705 A2 | 10/2004 |
| EP | 1474105 A2 | 11/2004 |
| EP | 1605976 A1 | 12/2005 |
| EP | 2429291 A1 | 3/2012 |
| EP | 1501467 B1 | 5/2012 |
| EP | 2238127 B1 | 8/2012 |
| EP | 2238128 B1 | 8/2012 |
| EP | 2228065 B1 | 12/2012 |
| EP | 2797556 A1 | 11/2014 |
| EP | 2861254 A2 | 4/2015 |
| EP | 3100728 A1 | 12/2016 |
| EP | 2999461 A4 | 2/2017 |
| EP | 2714011 B1 | 1/2018 |
| EP | 1951210 B1 | 12/2018 |
| WO | 9921829 A1 | 5/1999 |
| WO | 03020240 A2 | 3/2003 |
| WO | 03059318 A2 | 7/2003 |
| WO | 2004082716 A1 | 9/2004 |
| WO | 2007053393 A2 | 5/2007 |
| WO | 2010132711 A1 | 11/2010 |
| WO | 2012167212 A3 | 2/2013 |
| WO | 2013185764 A2 | 12/2013 |
| WO | 2014133539 A1 | 9/2014 |
| WO | 2014143108 A1 | 9/2014 |
| WO | 2014186843 A1 | 11/2014 |

OTHER PUBLICATIONS

Co-Pending U.S. Appl. No. 16/103,815, Restriction Requirement dated Dec. 13, 2018, 6 pages.
Co-pending U.S. Appl. No. 16/376,706, Final Office Action dated Mar. 27, 2020, 12 pages.
Co-pending U.S. Appl. No. 16/376,706, Non-final Office Action dated Nov. 12, 2019, 12 pages.
Co-pending U.S. Appl. No. 16/376,706, Notice of Allowance and Examiner Initiated Interview Summary dated Jun. 10, 2020, 8 pages.
Co-pending U.S. Appl. No. 16/376,706, Response to Mar. 27, 2020 Final Office Action dated May 27, 2020, 11 pages.
Co-pending U.S. Appl. No. 16/376,706, Response to Nov. 12, 2019 Non-Final Office Action filed Feb. 12, 2020, 10 pages.
Co-Pending U.S. Appl. No. 16/693,310, Final Office Action dated Sep. 3, 2021, 20 pages.
Co-Pending U.S. Appl. No. 16/693,310, Non-Final Office Action dated Feb. 7, 2020, 12 pages.
Co-Pending U.S. Appl. No. 16/693,310, Non-Final Office Action dated Jul. 21, 2022, 16 pages.
Co-Pending U.S. Appl. No. 16/693,310, Notice of Allowance dated Mar. 9, 2023, 7 pages.
Co-Pending U.S. Appl. No. 16/693,310, Petition Decision dated Mar. 29, 2021, 2 pages.
Co-Pending U.S. Appl. No. 16/693,310, Response to Feb. 7, 2020 Non-Final Office Action, filed May 5, 2020, 20 pages.
Co-Pending U.S. Appl. No. 16/693,310, Response to Jul. 21, 2022 Non-Final Office Action including Rule 132 Affidavit, dated Jan. 20, 2023, 15 pages.
Co-Pending U.S. Appl. No. 16/693,310, Response to Sep. 3, 2021 Final Office Action, dated Feb. 3, 2022, 7 pages.
Co-Pending U.S. Appl. No. 16/693,312, Final Office Action dated Mar. 29, 2021, 14 pages.
Co-Pending U.S. Appl. No. 16/693,312, Final Office Action dated Oct. 14, 2022, 16 pages.
Co-Pending U.S. Appl. No. 16/693,312, Non-Final Office Action dated Jan. 7, 2022, 15 pages.
Co-Pending U.S. Appl. No. 16/693,312, Non-Final Office Action dated Oct. 20, 2020, 17 pages.
Co-Pending U.S. Appl. No. 16/693,312, Response to Jan. 7, 2022 Non-Final Office Action, dated Jul. 6, 2022, 8 pages.
Co-Pending U.S. Appl. No. 16/693,312, Response to Mar. 29, 2021 Final Office Action, filed Sep. 29, 2021, 13 pages.
Co-Pending U.S. Appl. No. 16/693,312, Response to Oct. 14, 2022 Final Office Action dated Apr. 14, 2023, 16 pages.
Co-Pending U.S. Appl. No. 16/693,312, Response to Oct. 20, 2020 Non-Final Office Action, filed Feb. 22, 2021, 11 pages.
Co-Pending U.S. Appl. No. 16/849,099, Final Office Action dated Feb. 3, 2021, 24 pages.
Co-Pending U.S. Appl. No. 16/849,099, Non-Final Office Action dated Jul. 9, 2020, 19 pages.
Co-Pending U.S. Appl. No. 16/849,099, Notice of Abandonment, Aug. 20, 2021, 2 pages.
Co-Pending U.S. Appl. No. 16/849,099, Response to Jul. 9, 2020 Non-Final Office Action, dated Dec. 9, 2020, 10 pages.
Co-Pending U.S. Appl. No. 16/863,567, Advisory Action dated Dec. 30, 2021, 11 pages.
Co-Pending U.S. Appl. No. 16/863,567, Final Office Action dated Dec. 28, 2020, 17 pages.
Co-Pending U.S. Appl. No. 16/863,567, Final Office Action dated Oct. 26, 2021, 11 pages.
Co-Pending U.S. Appl. No. 16/863,567, Non-Final Office Action and Examiner Initiated Interview Summary dated Jun. 9, 2021, 14 pages.
Co-Pending U.S. Appl. No. 16/863,567, Non-Final Office Action dated Jun. 4, 2020, 18 pages.
Co-Pending U.S. Appl. No. 16/863,567, Response to Jun. 4, 2020 Non-Final Office Action dated Dec. 4, 2020, 10 pages.
Co-Pending U.S. Appl. No. 16/863,567, Response to Jun. 9, 2021 Non-Final Office Action dated Oct. 12, 2021, 8 pages.
Co-Pending U.S. Appl. No. 16/863,567, Response to May 13, 2020 Restriction Requirement, filed May 26, 2020, 44 pages.
Co-Pending U.S. Appl. No. 16/863,567, Response to Oct. 26, 2021 Final Office Action, dated Dec. 10, 2021, 8 pages.
Co-Pending U.S. Appl. No. 16/863,567, Restriction Requirement dated May 13, 2020, 5 pages.
Co-Pending U.S. Appl. No. 16/946,941, Non-Final Office Action dated Feb. 7, 2022, 15 pages.
Co-Pending U.S. Appl. No. 16/946,941, Notice of Allowance dated Apr. 4, 2022, 9 pages.
Co-Pending U.S. Appl. No. 16/946,941, Preliminary Amendment filed Jan. 20, 2021, 3 pages.
Co-Pending U.S. Appl. No. 16/946,941, Response to Feb. 7, 2022 Non-Final Office Action, dated Mar. 8, 2022, 6 pages.
Co-Pending U.S. Appl. No. 17/306,490, Preliminary Amendment filed Dec. 7, 2022, 38 pages.
Co-pending U.S. Appl. No. 17/566,840, Non-Final Office Action dated Mar. 23, 2022, 11 pages.
Co-pending U.S. Appl. No. 17/566,840, Notice of Allowance dated Jul. 25, 2022, 7 pages.
Co-pending U.S. Appl. No. 17/566,840, Notice of Allowance dated Nov. 9, 2022, 7 pages.
Co-pending U.S. Appl. No. 17/566,840, Petition Under 37 CFR 1.181 and Preliminary Amendment, dated Feb. 22, 2022, 9 pages.
Co-pending U.S. Appl. No. 17/566,840, Response to Mar. 23, 2022 Non-Final Office Action, dated Jul. 7, 2022, 10 pages.
Co-Pending U.S. Appl. No. 17/585,190, Preliminary Amendment dated Mar. 4, 2022, 4 pages.
Co-Pending U.S. Appl. No. 17/585,190, Restriction Requirement dated Oct. 19, 2023, 5 pages.
Co-Pending U.S. Appl. No. 17/861,226, Preliminary Amendment dated Jul. 10, 2022, 4 pages.
(Devlin, Jodi) Co-pending U.S. Appl. No. 17/566,840, filed Dec. 31, 2021, Specification, Claims, and Figures.
(Devlin, Jodi) Co-pending U.S. Appl. No. 18/107,785, filed Feb. 9, 2023, Specification, Claims, and Figures.
(Devlin, Jodi) Co-pending U.S. Appl. No. 18/121,980, filed Mar. 15, 2023, Specification, Claims, and Figures.
(Ivaturi, Vijay et al.) U.S. Appl. No. 16/376,706, filed Apr. 5, 2019, Specification, Claims, Figures.
(Ivaturi, Vijay et al.) U.S. Appl. No. 16/549,620, filed Aug. 23, 2019, Specification, Claims, Figures and File History as of Dec. 2020, 77 pages (abandoned).

(56) References Cited

OTHER PUBLICATIONS (Ivaturi, Vijay et al.) U.S. Appl. No. 17/003,297, filed Aug. 26, 2020, Specification, Claims, Figures.
(Ivaturi, Vijay et al.) U.S. Appl. No. 18/156,092, filed Jan. 18, 2023, Specification, Claims, Figures.
(Kashfian, Brandon Ira) Co-Pending U.S. Appl. No. 18/126,561, filed Mar. 27, 2023, Specification and Claims.
(Kashfian, Brandon Ira) Co-Pending U.S. Appl. No. 18/135,467, filed Apr. 17, 2023, Specification and Claims.
(Kashfian, Brandon Ira) Co-Pending U.S. Appl. No. 18/304,196, filed Apr. 20, 2023, Specification and Claims.
(Kashfian, Brandon Ira) Co-Pending U.S. Appl. No. 18/306,660, filed Apr. 25, 2023, Specification and Claims.
(Kashfian, Brandon Ira) Co-Pending U.S. Appl. No. 18/315,790, filed May 11, 2023, Specification and Claims.
(Kashfian, Brandon Ira) Co-Pending U.S. Appl. No. 18/321,220, filed May 22, 2023, Specification and Claims.
(Kashfian, Brandon Ira) Co-Pending U.S. Appl. No. 18/323,337, filed May 24, 2023, Specification and Claims.
(Kashfian, Brandon Ira) Co-Pending U.S. Appl. No. 18/324,703, filed May 26, 2023, Specification and Claims.
(Somberg, John C. et al.) Co-Pending U.S. Appl. No. 16/103,815, filed Aug. 14, 2018, Specification, Claims, Figures.
(Somberg, John C. et al.) Co-Pending U.S. Appl. No. 16/693,310, filed Nov. 24, 2019, Specification, Claims, Figures.
(Somberg, John C. et al.) Co-Pending U.S. Appl. No. 16/693,312, filed Nov. 24, 2019, Specification, Claims, Figures.
(Somberg, John C. et al.) Co-Pending U.S. Appl. No. 16/726,361, filed Dec. 24, 2019, Specification, Claims, Figures.
(Somberg, John C. et al.) Co-Pending U.S. Appl. No. 17/861,226, filed Jul. 10, 2022, Specification, Claims, Figures.
(Somberg, John C. et al.) Co-Pending U.S. Appl. No. 18/322,111, filed May 23, 2023, Specification, Claims, Figures.
(Somberg, John) Co-Pending U.S. Appl. No. 16/849,099, filed Apr. 15, 2020, Specification and Claims.
(Somberg, John) Co-Pending U.S. Appl. No. 16/863,567, filed Apr. 30, 2020, Specification and Claims.
(Somberg, John) Co-Pending U.S. Appl. No. 16/946,941, filed Jul. 13, 2020, Specification and Claims.
(Somberg, John) Co-Pending U.S. Appl. No. 17/306,490, filed May 3, 2021, Specification and Claims.
(Somberg, John) Co-Pending U.S. Appl. No. 17/585,190, filed Jan. 26, 2022, Specification and Claims.
(Somberg, John) Co-Pending U.S. Appl. No. 17/725,189, filed Apr. 20, 2022, Specification and Claims.
Amiodarone HCI injection for intravenous use [package insert], Lake Forest, IL: Hospira, Inc.; Initial U.S. Approval: 1995, 4 pages.
U.S. Appl. No. 17/003,297, Final Office Action dated Jul. 27, 2022, 16 pages.
U.S. Appl. No. 17/003,297, Non-Final Office Action dated Mar. 14, 2022, 14 pages.
U.S. Appl. No. 17/003,297, Notice of Allowance dated Oct. 18, 2022, 7 pages.
U.S. Appl. No. 17/003,297, Preliminary Amendment filed Dec. 8, 2020, 9 pages.
U.S. Appl. No. 17/003,297, Response to Final Office Action dated Sep. 27, 2022, 12 pages.
U.S. Appl. No. 17/003,297, Response to Mar. 14, 2022 Non-Final Office Action, dated Jun. 15, 2022, 12 pages.
Barbey, J.T. "Pharmacokinetic, pharmacodynamic, and safety evaluation of an accelerated dose titration regimen of sotalol in healthy middle-aged subjects," Clinical Pharmacology and Therapeutics vol. 66(1) (1999) 91-99.
Bashir, Y. et al., "Electrophysiologic profile and efficacy of intravenous dofetilide (UK-68,798), a new class III antiarrhythmic drug, in patients with sustained monomorphic ventricular tachycardia" The American Journal of Cardiology, vol. 76, Issue 14, Nov. 15, 1995, pp. 1040-1044, abstract.
Batra, Anjan S., et al., "Junctional ectopic tachycardia: Current strategies for diagnosis and management," Progress in Pediatric Cardiology, 35 (2013) 49-54.
Batul, S.A., "Intravenous sotalol: Reintroducing a forgotten agent to the electrophysiology therapeutic arsenal," J. Atrial Fibrillation vol. 9(3) (Feb.-Mar. 2017) 1-5.
Blair, Andrew D., et al., Sotalol kinetics in renal insufficiency, Clin. Pharmacol. Ther., 457-463 (Apr. 1981) (7 pages).
Boriani, G. et al., Increase in QT/QTc dispersion after low energy cardioversion of chronic persistent atrial fibrillation. International Journal of Cardiology. 2004; 95, 245-250.
Borquez, Alejandro A., et al., "Intravenous Sotalol in the Young, Safe and Effective Treatment With Standardized Protocols," JACC: Clinical Elecrophysiology, vol. 6, No. 4, Apr. 2020:425-32 (2020).
Campbell, T.J., "Intravenous sotalol for the treatment of atrial fibrillation and flutter after cardiopulmonary bipass comparison with disopyramide and digoxin in a randomised trial," BR Heart J. (1985) 54:86-90.
Cantillon, D. J. and Amuthan, R. "Atrial Fibrillation", Cleveland Clinic: Center for Continuing Education, Disease Management: https://www.clevelandclinicmeded.com/medicalpubs/diseasemanagement/cardiology/atrial-fibrillation/, Aug. 2018, 18 pages.
Choc Children's, "Junctional Ectopic Tachycardia (JET) Care Guideline for Cardiovascular Intensive Care Unit (CVICU)," Sep. 18, 2019.
Cilliers, Antionette M., et al., "Junctional ectopic tachycardia in six paediatric patients," Heart; 78:413-415 (1997).
Co-Pending U.S. Appl. No. 16/103,815, Final Office Action dated Aug. 13, 2019, 13 pages.
Co-Pending U.S. Appl. No. 16/103,815, Non-Final Office Action dated Feb. 6, 2019, 9 pages.
Co-Pending U.S. Appl. No. 16/103,815, Notice of Allowance dated Oct. 30, 2019, 12 pages.
Co-Pending U.S. Appl. No. 16/103,815, Response to Aug. 13, 2019 Final Office Action, filed Oct. 17, 2019, 10 pages.
Co-Pending U.S. Appl. No. 16/103,815, Response to Dec. 13, 2018 Restriction Requirement, filed Dec. 31, 2018, 3 pages.
Cordarone® (amiodarone HCI) Tablets [package insert], Philadelphia, PA: Wyeth Pharmaceuticals Inc.; 2004, 29 pages.
Dahmane, E., "Clinical Pharmacology-Driven Research to Optimize Bedside Therapeutics of Sotalol Therapy," Clin Transl Sci (2019) 12:648-656.
Dumas, M. et al., "Variations of sotalol kinetics in renal insufficiency", International Journal of Clinical Pharmacology, Therapy, and Toxicology, Oct. 1, 1989, 27(10), Abstract only.
El-Assaad, I, "Lone Pediatric Atrial Fibrillation in the United States: Analysis of Over 1500 Cases," Pediatr. Cardiol. 38:1004-1009, Springer Publishing, United States (2017).
FDA Highlights of Prescribing Information sotalol hydrochloride injection (2009), https://www.accessdata.fda.gov/drugsatfda_docs/label/2009/022306s000lbl.pdf.
FDA Highlights of Prescribing Information Sotylize (sotalol hydrochloride (2014), https://www.accessdata.fda.gov/drugsatfda_docs/label/2014/205108s000lbl.pdf.
FDA "Highlights of Prescribing Information" for sotalol hydrochloride injection, Revised Mar. 2020, 16 pages, https://www.accessdata.fda.gov/drugsatfda_docs/label/2020/022306s005lblrpl.pdf.
Flecainide Acetate Tablets, USP [package insert], Jacksonville, FL: Ranbaxy Pharmaceuticals Inc.; 2003, 17 pages.
Galloway, C.D., "Development and Validation of a Deep-Learning Model to Screen for Hyperkalemia From the Electrocardiogram," JAMA Cardiol.: E1-E9, Amer. Med. Assoc., United States (Apr. 3, 2019).
Gomes, J.A., "Oral d,l Sotalol reduces the incidence of postoperative atrial fibrillation in coronary artery bypass surgery patients: a randomized, double-blind, placebo-controlled study," J. Am. Coll. Cardio. 34(2):334-9 (1999).
Hannun, A.Y., "Cardiologist-level arrhythmia detection and classification in ambulatory electrocardiograms using a deep neural network," Nature Medicine 25:65-69, Nature Publishing (Jan. 2019).
Ho, D.S.W, et al., "Rapid intravenous infusion of d-l sotalol: time to onset of effects on ventricular refractoriness, and safety," European Heart J. 16:81-86, European Soc. of Cardiology, UK (1995).

(56) References Cited

OTHER PUBLICATIONS

Hoffman et al. "Renal Insufficiency and Medication in Nursing Homes" Medicine Deutsches Arzteblatt International 2016; 113: 92-98.

Ibutilide Fumarate Injection [package insert], Morgantown, WV: Mylan Institutional LLC; 2020, 14 pages.

Kerin, Nicholas A., "Intravenous Sotalol: an under used treatment strategy," Cardiology (2018) 140:143-145.

Laer, S., et al., "Development of a safe and effective pediatric dosing regimen for sotalol based population pharmacokinetics and pharmacodynamics in children with supraventricular tachycardia . . . " Pediatric Cardiology vol. 46(7) (2005) 1322-30.

Le Coz, F. et al. Pharmacokinetic and pharmacodynamic modeling of the effects of oral and intravenous administrations of dofetilide on ventricular repolarization. Clin Pharmacol Ther 1995; 57:533.

Learn the Heart, "Antiarrhythmic Drug Review," https://www.healio.com/cardiology/learn-the-heart/cardiology-review/topic-reviews/antiarrhythmic-drugs (Year: 2022).

Li, X, "Efficacy of intravenous sotalol for treatment of incessant tachyarrhythmias in children," Amer. J. of Cardiology (2017) 119:1366-1370.

Li, X., "Pediatric dosing of intravenous sotalol based on body surface area in patients with arrhythmia," Pediatr Cardiol (2017) 38:1450-1455.

Lynch, J.J., et al., "Prevention of ventricular fibrillation by dextrorotatory sotalol in conscious canine model of sudden coronary death," Amer. Heart J. vol. 109(5) Part 1, (1985) 949-958.

Maragnes, P., et al., "Usefulness of oral sotalol for the treatment of junctional ectopic tachycardia," Int'l J. of Cardiology, 35 (1995) 165-167.

Marill, K.A., "Meta-analysis of the risk of torsades de pointes in patients treated with intravenous racemic sotalol," Academic Emergency Medicine 8(2):117-124, Wiley, United States (2001).

Multaq (dronedarone) tablets, for oral use [package insert], Bridgewater, NJ: Sanofi-Aventis U.S. LLC; 2020, 24 pages.

Neumar, R.W., et al., "Part 8: Adult advanced cardiovascular life support," Circulation (2010) 122, suppl. 3, S729-S767.

Patel, A., "Is Sotalol more effective than standard beta-blockers for prophylaxis of atrial fibrillation during cardiac surgery?" Interactive CardioVascular and Thoracic Surgery 4 (2005) 147-50.

Peters, F.P.J., "Treatment of recent onset atrial fibrillation with intravenous sotalol and/or flecainide," Netherlands J. of Medicine 53:93-96, Elsevier Science B.B., Netherlands (1998).

Peters, N.S., "Post-cardioversion atrial fibrillation: the synthesis of modern concepts?" european Heart J. (2000) 21, 1119-1121.

Procainamide Dosage. Drugs.com. Last updated Sep. 13, 2021. 3 pages.

Procainamide Hydrochloride Injection, USP [package insert], Lake Forest, IL: Hospira, Inc.; 2021, 12 pages.

Radford, D.J., "Atrial Fibrillation in Children," Pediatrics 59(2):250-256, Amer. Acad. of Pediatrics, US (1977).

Rasmussen, H.S. et al., Dofetilide, A Novel Class III Antiarrhythmic Agent, J Cardiovasc Pharmacol. 1992;20 Suppl 2:S96-105.

Rosseau, M. F., Cardiac and Hemodynamic Effects of Intravenous Dofetilide in Patients With Heart Failure, Am J Cardiol 2001;87:1250-1254.

Rythmol (propafenone hydrochloride tablets), for oral use [package insert], Research Triangle Park, NC: GlaxoSmithKline; 2018, 24 pages.

Sanjuan, R., "Preoperative use of sotalol versus atenolol for atrial fibrillation after cardiac surgery," Ann Thorac Surg (2004) 77:838-43.

Saul, J.P., "Pharmacokinetics and pharmacodynamics of sotalol in a pediatric population with supraventricular and ventricular tachyarrhythmia," Clinical Pharma & Therapeutics 69(3): 145-157 (2001).

Sedgwick, M. et al., Pharmacokinetic and pharmacodynamic effects of UK-68,798, a new potential class III antiarrhythmic drug, Br. J. Clin. Pharmac. (1991), 31, 515-519.

Snider, M., et al., "Initial experience with antiarrhythmic medication monitoring by clinical pharmacists in an outpatient setting: a retrospective review," Clinical Therapeutics vol. 31(36) (2009) 1209-1218.

Somberg, et al., "Sotalol versus Amiodarone in Treatment of Atrial Fibrillation," J. Atrial Fibrillation, Feb.-Mar. 2016, vol. Issue 5.

Somberg, J.C., "Gender differences in cardiac repolarization following intravenous sotalol administration," J. Cardiovascular Pharmacology and Therapeutics (2012) 17(1) 86-92.

Somberg, J.C., "QT prolongation and serum sotalol concentration are highly correlated following intravenous and oral sotalol," Cardiology (2010) 116(3):219-25.

Somberg, J.C., et al., "Developing a safe intravenous sotalol dosing regimen," Amer. J. of Therapeutics 17(2010) 365-372.

Somberg, John et al. Model-Informed Development of Sotalol Loading and Dose Escalation Employing an Intravenous Infusion. Cardiol Res. 2020; 11(5):294-304.

Sundquist, H.K. et al., "Serum levels and half-life of sotalol in chronic renal failure", Annals of Clinical Research, Dec. 1, 1975, 7(6), Abstract Only.

Thomas, S.P., "Rapid loading of sotalol or amiodarone for management of recent onset symptomatic atrial fibrillation: A randomized, digoxin-controlled trial," Am. Heart J., 147(1) (6 pages) (2004).

Tikosyn® (dofetilide) Capsules [package insert], NY, NY: Pfizer Inc.; 2014, 30 pages.

Tse, H.F., "Atrial pacing for suppression of early reinitiation of atrial fibrillation after successful internal cardioversion," european Heart J. (2000) 21, 1167-1176.

U.S. Appl. No. 16/376,706 (U.S. Pat. No. 10,799,138), file history Dec. 2020, 151 pages.

Valdes, S.O., "Early experience with intravenous sotalol in children with and without congenital heart disease," Heart Rhythm 15(12): 1862-1869, Elsevier Inc., (Jul. 9, 2018).

Yarlagadda, B, et al., "Safety and efficacy of inpatient initiation of dofetilide versus sotalol for atrial fibrillation," J. Atrial Fibrillation vol. 101(4) (2017) 1-5.

(Kashfian, Brandon Ira et al.) Co-Pending U.S. Appl. No. 19/009,774), filed Jan. 3, 2025, Specification, Drawings, and Claims.

(Kashfian, Brandon Ira et al.) Co-Pending U.S. Appl. No. 19/080,585, filed Mar. 14, 2025, Specification and Claims.

(Kashfian, Brandon Ira) Co-Pending U.S. Appl. No. 18/631,538, filed Apr. 10, 2024, Specification and Claims.

(Somberg, John et al.) Co-Pending U.S. Appl. No. 19/019,556, filed Jan. 14, 2025, Specification and Claims.

(Somberg, John et al.) Co-Pending U.S. Appl. No. 19/022,878, filed Jan. 15, 2025, Specification and Claims.

(Somberg, John) Co-Pending U.S. Appl. No. 18/417,748, filed Jan. 19, 2024, Specification and Claims.

U.S. Appl. No. 18/156,092, Response to Notice to File Missing Parts and Preliminary Amendment, dated Apr. 4, 2023, 6 pages.

Brugada, J. et al., 2019 ESC Guidelines for the management of patients with supraventricular tachycardia, European Heart Journal (2020) 41, 655-720, 66 pages.

Co-Pending U.S. Appl. No. 16/693,312, Final Office Action dated Feb. 22, 2024, 23 pages.

Co-Pending U.S. Appl. No. 16/693,312, Interview Summary dated Feb. 22, 2024, 1 page.

Co-Pending U.S. Appl. No. 16/693,312, Non-Final Office Action dated Aug. 19, 2024, 15 pages.

Co-Pending U.S. Appl. No. 16/693,312, Non-Final Office Action dated Nov. 1, 2023, 18 pages.

Co-Pending U.S. Appl. No. 16/693,312, Notice of Allowance dated Apr. 15, 2025, 9 pages.

Co-Pending U.S. Appl. No. 16/693,312, Response to Aug. 19, 2024 Non-Final Office Action, dated Dec. 19, 2024, 8 pages.

Co-Pending U.S. Appl. No. 16/693,312, Response to Feb. 22, 2024 Final Office Action, dated May 14, 2024, 10 pages.

Co-Pending U.S. Appl. No. 16/693,312, Response to Nov. 1, 2023 Non-Final Office Action, dated Feb. 1, 2024, 11 pages.

Co-Pending U.S. Appl. No. 16/693,312, Rule 132 Affidavit dated Feb. 1, 2024, 7 pages.

(56) References Cited

OTHER PUBLICATIONS

Co-Pending U.S. Appl. No. 17/306,490, Final Office Action dated Mar. 11, 2025, 13 pages.
Co-Pending U.S. Appl. No. 17/306,490, Non-Final Office Action dated Jun. 7, 2024, 50 pages.
Co-Pending U.S. Appl. No. 17/306,490, Response to Jun. 7, 2024 Non-Final Office Action, dated Dec. 6, 2024, 9 pages.
Co-Pending U.S. Appl. No. 17/725,189, Non-Final Office Action dated Jun. 18, 2024, 10 pages.
Co-Pending U.S. Appl. No. 17/725,189, Notice of Allowance dated Apr. 30, 2025, 9 pages.
Co-Pending U.S. Appl. No. 17/725,189, Response to Jun. 18, 2024 Non-Final Office Action, dated Dec. 18, 2024, 5 pages.
Co-Pending U.S. Appl. No. 17/861,226, Final Office Action dated Mar. 21, 2025, 24 pages.
Co-Pending U.S. Appl. No. 17/861,226, Interview Summary dated Jan. 7, 2025, 2 pages.
Co-Pending U.S. Appl. No. 17/861,226, Non-Final Office Action dated Jul. 16, 2024, 17 pages.
Co-Pending U.S. Appl. No. 17/861,226, Response to Jul. 16, 2024 Non-Final Office Action, dated Dec. 16, 2024, 9 pages.
Co-pending U.S. Appl. No. 18/107,785, Non-Final Office Action dated May 8, 2025, 9 pages.
Co-pending U.S. Appl. No. 18/107,785, Preliminary Amendment dated Feb. 15, 2024, 10 pages.
Co-pending U.S. Appl. No. 18/121,980, Preliminary Amendment dated Jul. 18, 2023, 6 pages.
Co-Pending U.S. Appl. No. 18/322,111, Preliminary amendment dated Jan. 31, 2024, 7 pages.
Co-Pending U.S. Appl. No. 18/417,748, Preliminary Amendment dated Apr. 22, 2024, 6 pages.
Co-Pending U.S. Appl. No. 19/019,556, Preliminary Amendment dated Jan. 14, 2025, 4 pages.
Dwivedi, S.K. et al. "Efficacy of Dual Strategy of Sotalol and Electrical Cardioversion With Balloon Mitral Valvotomy in Persistent Rheumatic Atrial Fibrillation With Mitral Stenosis," Heart, 2012, 98 (Suppl 2): E1-E319, 2 pages.
Falk, Rodney H. et al., Intravenous Dofetilide, a Class III Antiarrhythmic Agent, for the Termination of Sustained Atrial Fibrillation or Flutter, JACC vol. 29, No. 2, 385-90 (Feb. 1997).
Frost, L. et al., Efficacy and safety of dofetilide, a new class III antiarrhythmic agent, in acute termination of atrial fibrillation or flutter after coronary artery bypass surgery, International Journal of Cardiology, 58 (1997) 135-140, 6 pages.
Kennedy, D. et al. "Efficacy and Safety of Single Day Loading of Intravenous Sotalol Prior to Direct Current Cardioversion for the Termination of Cardiac Atrial Arrhythmias: An Observational Study," Heart Rhythm, vol. 19, No. 5, May Supplement 2022, 2 pages.
Kerin, N. Z. and Jacob, S., The Efficacy of Sotalol in Preventing Postoperative Atrial Fibrillation: A Meta-Analysis, The American Journal of Medicine, vol. 124, No. 9, Sep. 2011, 9 pages.

Kijtawornrat, A. et al., Assessment of QT-prolonging drugs in the isolated normal and failing rabbit hearts, The Journal of Toxicological Sciences, 2012, vol. 37, No. 3, 455-462.
Kobayashi, Y. et al. "Clinical and Electrophysiologic Effects of Dofetilide in Patients with Supraventricular Tachyarrhythmias", Journal of Cardiovascular Pharmacology, Sep. 1997, vol. 30, Issue 3, 367-373, 9 pages.
Lai, L. et al. "Intravenous Sotalol Decreases Transthoracic Cardioversion Energy Requirement for Chronic Atrial Fibrillation in Humans: Assessment of the Electrophysiological Effects by Biatrial Basket Electrodes," Journal of the American College of Cardiology, vol. 35, No. 6, 2000, 1435-1441, 8 pages.
Li, Xiaomei, Pediatric Dosing of Intravenous Sotalol Based on Body Surface Area in Patients with Arrhythmia, Pediatr Cardiol (2017) 38:1450-1455.
Lindeboom, J. et al. Efficacy and Safety of Intravenous Dofetilide for Rapid Termination of Atrial Fibrillation and Atrial Flutter, The American Journal of Cardiology, vol. 85, Apr. 15, 2000, 1031-1033, 3 pages.
Malloy-Walton, L. E. et al. "IV Sotalol Use in Pediatric and Congenital Heart Patients: A Multicenter Registry Study," Journal of the American Heart Association, 2022, 11:e024375, 8 pages.
Norgaard, B. et al., Efficacy and safety of intravenously administered dofetilide in acute termination of atrial fibrillation and flutter: A multicenter, randomized, double-blind, placebo-controlled trial, American Heart Journal, (1999) vol. 137, No. 6, pp. 1062-1069, 8 pages.
Tham, T. C. K., et al., Pharmacodynamics and Pharmacokinetics of the Class III Antiarrythmic Agent Dofetilide (UK-68,798) in Humans, Journal of Cardiovascular Pharmacology, 21:507-512, 1993, 6 pages.
Valdes, S. O. et al. "Intravenous Sotalol for Acute Conversion of Intra-Atrial-Reentrant-Tachycardia in Adults with Congenital Heart Disease," Heart Rhythm, vol. 19, No. 5, May Supplement 2022, 2 pages.
Valdes, S.O. et al. "Intravenous sotalol for the management of postoperative junctional ectopic tachycardia," Heart Rhythm Case Reports, vol. 4, No. 8, Aug. 2018, 375-377, 3 pages.
Von Bergen, N. H. et al. "Outpatient intravenous sotalol load to replace 3-day admission oral sotalol load", Heart Rhythm Case Reports (Jul. 2019), vol. 5, issue 7, p. 382-383.
Woosley, R., Therapeutic use of dofetilide, UpToDate, Inc., Wolters Kluwer, 2020, 17 pages.
(Kashfian, Brandon Ira et al.) Co-Pending U.S. Appl. No. 19/277,199, filed Jul. 22, 2025, Specification and Claims.
Co-Pending U.S. Appl. No. 17/306,490, Non-Final Office Action dated Jul. 15, 2025, 12 pages.
Co-Pending U.S. Appl. No. 17/306,490, Response to Mar. 11, 2025 Final Office Action, dated Jun. 26, 2025, 6 pages.
Co-Pending U.S. Appl. No. 17/861,226, Response to Mar. 21, 2025 Final Office Action, dated Jun. 23, 2025, 11 pages.

\* cited by examiner

ANTI-ARRHYTHMIC COMPOSITIONS AND METHODS

CROSS-REFERENCE TO RELATED APPLICATIONS

This application is a Continuation-in-Part application of U.S. application Ser. No. 17/566,840 filed Dec. 31, 2021, which application relies on the disclosure of and claims priority to and the benefit of the filing date of U.S. Provisional Application Nos. 63/235,500 filed Aug. 20, 2021 and 63/276,947 filed Nov. 8, 2021. The present application relies on the disclosure of and claims priority to and the benefit of the filing date of U.S. Provisional Application Nos. 63/235,500 filed Aug. 20, 2021, 63/276,947 filed Nov. 8, 2021, 63/331,905 filed Apr. 18, 2022, 63/334,267 filed Apr. 25, 2022, 63/340,581 filed May 11, 2022, 63/344,154 filed May 20, 2022, and 63/345,068 filed May 24, 2022, which applications are hereby incorporated by reference herein in their entireties.

FIELD OF THE INVENTION

The present disclosure is directed to the field of cardiovascular pharmaceutics, more particularly compositions and methods for the treatment of cardiovascular conditions such as arrhythmias with intravenous anti-arrhythmics, such as dofetilide.

BACKGROUND

Dofetilide is a class III antiarrhythmic agent which acts through blocking cardiac ion channels of the rapid component of the delayed rectifier potassium current Ikr. The agent, a sulfonamide, is approved to treat atrial fibrillation and atrial flutter. Dofetilide normalizes sinus rhythm by prolonging cardiac action potential duration and effective refractory period due to delayed repolarization without affecting conduction velocity. Dofetilide is currently approved in the US for oral administration under the brand name TIKOSYN® (Pfizer Inc., New York, NY). It is not approved for parenteral administration.

SUMMARY OF THE INVENTION

Described herein are methods of administering one or more anti-arrhythmic, such as a Class I or Class III anti-arrhythmic, for example dofetilide, to a patient in need thereof in an amount effective for treating a cardiovascular condition of the patient. In embodiments, the effective amount of anti-arrhythmic, such as dofetilide, can be administered intravenously over a duration of at least 1 hour, and/or can be administered intravenously as a loading dose of 0.1 to 12 µg/kg bodyweight over a duration of up to about 60 minutes, or more, and/or infused intravenously as a maintenance dose of 0.1 to 10 µg/kg/hr over a duration of at least 1 hour, and/or the dosing can be adjusted for pharmacokinetics of the particular drug being administered, such as for dofetilide or other anti-arrhythmics, including sotalol, amiodarone, ibutilide, dronedarone, procainamide, flecainide, or propafenone.

The cardiovascular condition can include atrial fibrillation, atrial flutter, ventricular tachycardia, hemodynamically stable or unstable ventricular tachycardia, ventricular fibrillation, paroxysmal supraventricular tachycardia, paroxysmal atrial fibrillation, heart failure, coronary artery disease, pulmonary artery hypertension, atrial tachycardia, junctional ectopic tachycardia, or junctional tachycardia. The method can further include measuring a QT interval (or QTc) of the patient before, during, and/or after the administering, and selecting or adjusting the effective amount, the loading dose and/or the maintenance dose based on the QT interval or QTc at any point during administering the protocol. The method can further include measuring a creatinine clearance of the patient before the administering, and selecting or adjusting the effective amount, the loading dose and/or the maintenance dose based on the creatinine clearance.

Compositions for intravenous administration of anti-arrhythmics, including dofetilide, are also provided. The compositions and methods are particularly useful for situations in which oral administration is impractical, such as gastrointestinal conditions affecting drug absorption, recovery from gastrointestinal surgery, and/or intensive care, or where oral administration is not recommended or possible (NPO).

DETAILED DESCRIPTION

Reference will now be made in detail to various illustrative implementations. It is to be understood that the following discussion of the implementations is not intended to be limiting.

AF is atrial fibrillation.
AFL is atrial flutter.
AF/AFL=atrial fibrillation and/or atrial flutter.
IV is intravenous.
PO means "per os" and refers to an oral dosing regimen.
BID means "bis in die" and means twice a day.
QD means "quaque die" and means once a day.
QID means "quater in die" and means four times a day.
Patient (or subject) refers to a human patient.
BP is blood pressure.
HR is heart rate.
Renally impaired refers to patients/subjects having creatinine clearance rates of ≤60 mL/min, such as ≤30 mL/min.
Cmax ss is the maximal concentration obtained at steady state.
QT is the interval measured from the start of the Q wave or the QRS complex, to the end of the T wave, where the Q wave corresponds to the beginning of ventricular depolarization and the T wave end corresponds to the end of ventricular repolarization.
QTc is the calculated interval that represents the QT interval corrected for heart rate and can be derived by mathematical correlation of the QT interval and the heart rate.
ΔQTc is the difference between a QTc measurement taken prior to the start of treatment and a QTc measured after the start of treatment (e.g., during loading or maintenance).

The terms "treat," "treating," and "treatment" refer to any indicia of success in the treatment or amelioration of an injury, disease, or condition, including any objective or subjective parameter such as abatement; remission; diminishing of symptoms or making the injury disease, or condition more tolerable to the subject; slowing in the rate of degeneration or decline; or improving a subject's physical or mental well-being. The treatment or amelioration of symptoms can be based on objective or subjective parameters, including the results of a physical examination, neuropsychiatric examinations, or psychiatric evaluation.

Hospital refers to a medical facility staffed and equipped to provide continuous ECG monitoring and cardiac resuscitation to patients, if needed. Typically, the medical personnel are trained in the management of serious ventricular arrhythmias.

Escalation means increasing the dofetilide dosage of a patient already receiving dofetilide, for example where a subject is currently taking a specific amount of an oral dose and escalation involves administering one or more IV doses to escalate the subject to a higher target oral dose.

The term "about" used herein in the context of quantitative measurements means the indicated amount±10%. For example, "about 2 mg" can mean 1.8-2.2 mg.

Formulations

Formulations for parenteral administration of anti-arrhythmics, such as dofetilide, can include sterile aqueous or non-aqueous solutions, suspensions, and emulsions. Formulations for other anti-arrhythmics, including sotalol, amiodarone, ibutilide, dronedarone, procainamide, flecainide, or propafenone can be similar. Parenteral administration of the formulation, if used, is generally characterized by injection and can include subcutaneous, intramuscular, intravenous, intradermal, intrathecal, and epidural administration. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Dofetilide (CAS Registry No. 115256-11-6; Pub Chem ID 71329) has a molecular weight of 441.6 g/mol. According to PubChem, dofetilide is soluble in 0.1M NaOH, acetone, and 0.1M HCl, and very slightly soluble in propan-2-ol. It is also very slightly soluble in water. The molecular structure is shown below:

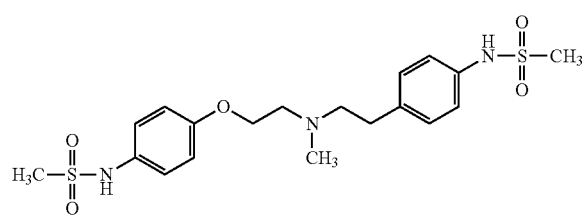

Dofetilide can be formulated in vehicles suitable for intravenous administration, such as those described in Remington: The Science and Practice of Pharmacy (19th ed.) ed. A. R. Gennaro, Mack Publishing Company, Easton, Pa. 1995, which is incorporated by reference herein in its entirety. Typically, an appropriate amount of a pharmaceutically-acceptable salt is used in the formulation to render the formulation isotonic. Examples of the pharmaceutically-acceptable carrier include, but are not limited to, sterile aqueous solutions such as saline, Ringer's solution and dextrose solution. The pH of the solution can be from about 4 to about 8, such as from about 4.5 to about 6.5, about 5 to about 6, or about 7 to about 7.5, and can be adjusted with appropriate amounts of acid, base, and/or buffering agent. Examples of suitable acids include, but are not limited to, hydrochloric acid, lactic acid, citric acid, acetic acid, and phosphoric acid. An example of a suitable base includes sodium hydroxide. Examples of buffering agents include acetic acid/acetate and bicarbonate/carbonate. If aqueous solubility is poor, intravenous emulsifying agents such as CREMOPHOR® EL (polyoxyethylated castor oil, CrEL) can be also be used.

Dofetilide can be formulated in aqueous or non-aqueous solutions, suspensions, or emulsions for intravenous administration at a concentration of 1-1000 µg/mL, including 1, 2, 5, 10, 15, 20, 25, 30, 35, 40, 45, 50, 55, 60, 65, 70, 75, 80, 90, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000 µg/mL, 10-100 µg/mL, 20-80 µg/mL, 30-70 µg/mL, or 40-60 µg/mL.

Compositions for oral administration of the anti-arrhythmics, if desired, include powders or granules, suspensions or solutions in water or non-aqueous media, capsules, sachets, or tablets. Thickeners, flavorings, diluents, emulsifiers, dispersing aids or binders may be desirable. Pharmaceutically acceptable carriers include fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethylstarch, cross-linked polyvinyl pyrrolidone, agar, or alginic acid or a salt thereof, such as sodium alginate. Auxiliaries, flow-regulating agents and lubricants, such as silica, talc, stearic acid or salts thereof, such as magnesium stearate or calcium stearate, and/or polyethylene glycol can be added. In one implementation, dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Slow dissolving polymers such as poly(bis(p-carboxyphenoxy)-propane:sebacic acid—CCP:SA) may also be used to generate wafers or beads that control or time the release of the composition. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules or nanoparticles which may optionally be mixed with fillers such as lactose, binders such as starches, and/or lubricants such as talc or magnesium stearate and, optionally, stabilizers. The active compound can be dissolved or suspended in suitable liquids, such as fatty oils, or liquid paraffin, optionally with stabilizers. LABRASOL®, a PEG derivative of medium chain fatty acid triglycerides of capric and caprylic acid, can be used as a pharmaceutical carrier and solubilizing agent to increase oral bioavailability if water solubility is poor.

Dofetilide is currently formulated and marketed as TIKOSYN® capsules containing the following inactive ingredients: microcrystalline cellulose, corn starch, colloidal silicon dioxide and magnesium stearate. TIKOSYN® is supplied for oral administration in three dosage strengths: 125 mcg (0.125 mg) orange and white capsules, 250 mcg (0.25 mg) peach capsules, and 500 mcg (0.5 mg) peach and white capsules.

Dofetilide has been experimentally infused intravenously in patients in pharmacokinetic and pharmacodynamic studies (see H. S. Rasmussen et al., Dofetilide, A Novel Class III Antiarrhythmic Agent, J Cardiovasc Pharmacol. 1992; 20 Suppl 2:S96-105 and M. Sedgwick et al., Pharmacokinetic and pharmacodynamic effects of UK-68,798, a new potential class III antiarrhythmic drug, Br. J. Clin. Pharmac. (1991), 31, 515-519 ("Sedgwick et al., 1991") each incorporated by reference herein in its entirety). Sedgwick formulated dofetilide as a free base in a liquid vehicle containing 50 mg/ml mannitol and 4 mg/ml citric acid, titrated to pH 3.5 with sodium hydroxide. Sedgwick found dofetilide "easily soluble in aqueous solution". Another investigator formulated dofetilide in 5% glucose as diluent (see M. F. Rousseau, Cardiac and Hemodynamic Effects of Intravenous Dofetilide in Patients With Heart Failure, Am J Cardiol 2001; 87:1250-1254). Various examples of IV formulations of dofetilide using vehicles containing one or more of 1,3-propanediol, HCl, acetic acid, sodium acetate, N,N-Dimethylacetamide, D-glucose and water, at a pH ranging from 4 to 7 have been described. (US Patent Application Publication No. 20190388371A1, incorporated by reference herein in its entirety). The dofetilide concentration was generally 50 µg/mL. Liposomal compositions for intravenous administration which include dofetilide have been described (see U.S. Pat. No. 9,682,041B2).

Intravenous Administration

First order kinetics with a linear dose plasma concentration relationship, and a linear relationship between plasma concentration and effect on QT interval during IV administration of dofetilide have been described. (Sedgwick et al., 1991). Such kinetics allows titration of an appropriate anti-arrhythmic therapeutic plasma concentration and effect. The elimination half-life is approximately ten hours after intravenous or oral administration, and elimination is primarily renal (80 percent). Clearance has been estimated to be 0.35 L/hour/kg (Le Coz F, et al. Pharmacokinetic and pharmacodynamic modeling of the effects of oral and intravenous administrations of dofetilide on ventricular repolarization. Clin Pharmacol Ther 1995; 57:533).

According to embodiments, Aspect 1 is a method comprising: administering an anti-arrhythmic, such as dofetilide, to a patient, wherein the anti-arrhythmic or dofetilide is administered intravenously over a duration of at least 1 hour and in an amount effective for treating or preventing a cardiovascular condition of the patient.

Aspect 2 is a method, comprising: administering an anti-arrhythmic or dofetilide to a patient; wherein the anti-arrhythmic or dofetilide is administered: as a loading dose intravenously, optionally over a duration of up to 60 minutes, and in an amount ranging from 0.1 to 12 µg/kg bodyweight; and/or as a maintenance dose intravenously, optionally over a duration of at least 1 hour, and in an amount ranging from 0.1 to 10 µg/kg/hr, optionally alternatively or in addition wherein the amount of the IV loading dose is in the range of about ±50% of the IV maintenance dose.

Aspect 3 is the method of Aspect 1 or 2, wherein: the cardiovascular condition is selected from atrial fibrillation, atrial flutter, ventricular tachycardia, ventricular fibrillation, paroxysmal supraventricular tachycardia, heart failure, coronary artery disease, and pulmonary artery hypertension.

Aspect 4 is the method of any of Aspects 1-3, further comprising measuring a QT interval of the patient before, during, and/or after the administering, and selecting or adjusting the effective amount, the loading dose and/or the maintenance dose based on the QT interval.

Aspect 5 is the method of any of Aspects 1-4, further comprising measuring a creatinine clearance of the patient before the administering, and selecting or adjusting the effective amount, the loading dose and/or the maintenance dose based on the creatinine clearance.

Aspect 6 is a method of administering an anti-arrhythmic or dofetilide to a patient, comprising: (A) determining a creatinine clearance of the patient; (B) administering to the patient an IV loading dose of the anti-arrhythmic or dofetilide selected from an amount ranging from 0.1-12 µg/kg; (C) administering to the patient one or more IV maintenance dose of the anti-arrhythmic or dofetilide selected from an amount ranging from 0.1-10 µg/kg; and (D) optionally alternatively or in addition wherein the amount of the IV loading dose is in the range of about ±50% of the IV maintenance dose.

Aspect 7 is the method of any of Aspects 1-6, wherein the IV loading dose is 0.1 µg/kg, 0.5 µg/kg, 0.8 µg/kg, 1.5 µg/kg, 3.5 µg/kg, 4.5 µg/kg, 5.5 µg/kg, 6 µg/kg, 6.5 µg/kg, 7 µg/kg, 7.5 µg/kg, 8.5 µg/kg, 9 µg/kg, 9.5 µg/kg, 10.5 µg/kg, 11 µg/kg, or 11.5 µg/kg.

Aspect 8 is the method of any of Aspects 1-7, wherein the IV maintenance dose is 0.1 µg/kg, 0.5 µg/kg, 0.8 µg/kg, 1.5 µg/kg, 3.5 µg/kg, 4.5 µg/kg, 5.5 µg/kg, 6 µg/kg, 6.5 µg/kg, 7 µg/kg, 7.5 µg/kg, 8.5 µg/kg, 9 µg/kg, 9.5 µg/kg.

Aspect 9 is the method of any of Aspects 1-8, wherein the IV maintenance dose is lower than the IV loading dose.

Aspect 10 is the method of any of Aspects 1-8, wherein the IV maintenance dose is higher than the IV loading dose.

Aspect 11 is the method of any of Aspects 1-10, further comprising administering one or more oral dose of the anti-arrhythmic or dofetilide to the patient.

Aspect 12 is the method of any of Aspects 1-11, further comprising a time delay between completion of the administering of the IV loading dose and administering the one or more IV maintenance dose to the patient and/or administering the one or more oral dose to the patient.

Aspect 13 is the method of Aspect 12, wherein the time delay is less than 1 hour.

Aspect 14 is the method of Aspect 12, wherein the time delay is 1, 2, 3, 4, 5, or 6 hours.

Aspect 15 is the method of any of Aspects 1-8, wherein the IV maintenance dose is the same as the IV loading dose.

Aspect 16 is the method of Aspect 12, wherein the time delay is less than 30 minutes.

Aspect 17 is the method of any of Aspects 1-16, wherein the patient is being treated for atrial fibrillation and/or atrial flutter.

Aspect 18 is a method of administering an anti-arrhythmic or dofetilide to a patient, comprising: (A) determining a creatinine clearance of the patient; (B) administering to the patient an IV loading dose of the anti-arrhythmic or dofetilide selected from an amount ranging from 0.1-12 µg/kg; (C) administering to the patient (i) one or more IV maintenance dose of the anti-arrhythmic or dofetilide selected from an amount ranging from 0.1-10 µg/kg and/or (ii) one or more oral maintenance dose of the anti-arrhythmic or dofetilide selected from an amount ranging from 125 µg to 500 such as 125 µg, 250 µg, or 500 µg; and (D) optionally alternatively or in addition wherein the amount of the IV loading dose is in the range of about ±50% of the oral dose and/or the IV maintenance dose.

Aspect 19 is the method of Aspect 18, wherein the creatinine clearance of the patient is >60 mL/min and the oral maintenance dose is 500 µg.

Aspect 20 is the method of Aspect 18, wherein the creatinine clearance of the patient is 40-60 mL/min and the oral maintenance dose is 250 µg.

Aspect 21 is the method of Aspect 18, wherein the creatinine clearance of the patient is 20-40 mL/min and the oral maintenance dose is 125 µg.

Aspect 22 is the method of Aspect 18, wherein the creatinine clearance of the patient is 20-60 mL/min and the IV loading dose is 3.5 µg/kg.

Aspect 23 is a method of initiating anti-arrhythmic or dofetilide treatment in a patient, comprising: (A) determining a creatinine clearance of the patient; (B) determining a QT interval of the patient; (C) administering to the patient an IV loading dose of an anti-arrhythmic or dofetilide selected from an amount ranging from 0.1-12 µg/kg; and (D) determining a second QT interval of the patient; (E) optionally administering one or more subsequent IV and/or oral doses of the anti-arrhythmic or dofetilide to the patient; (F) optionally alternatively or in addition wherein the amount of the IV loading dose is in the range of about ±50% of the subsequent IV dose and/or oral dose; and (G) optionally determining one or more subsequent QT interval of the patient between one or more of the subsequent IV and/or oral doses.

Aspect 24 is the method of Aspect 23, further comprising: determining a change in QT interval of the patient; and if the second QT interval has increased less than 15% over the first QT interval, then administering to the patient one or more IV maintenance dose selected from an amount ranging from 0.1-10 µg/kg and/or one or more oral maintenance dose selected from an amount of 125 µg, 250 µg, or 500 µg.

Aspect 25 is the method of any of Aspects 1-24, wherein the patient is experiencing or has been diagnosed with atrial fibrillation, atrial flutter, ventricular tachycardia, ventricular fibrillation, paroxysmal supraventricular tachycardia, heart failure, coronary artery disease, and/or pulmonary artery hypertension.

Aspect 26 is a method of initiating or escalating anti-arrhythmic or dofetilide treatment in a patient having atrial fibrillation or atrial flutter, comprising: (A) determining a creatinine clearance of the patient wherein the creatinine clearance of the patient is 20 to 60 mL/min; (B) determining a QT interval of the patient; (C) administering to the patient an IV loading dose of an anti-arrhythmic or dofetilide, wherein the IV loading dose is selected from an amount ranging from 0.1-1.6 µg/kg and wherein optionally the IV loading dose is administered over 5, 10, 15, 20, 30, 45, or 60 minutes, optionally by way of several IV doses; (D) determining a second QT interval of the patient; (E) administering one or more subsequent IV and/or oral doses of the anti-arrhythmic or dofetilide to the patient beginning immediately, from 1-6 hours, from 2-6 hours, or from 2-4 hours after completion of the administering of the IV loading dose; (F) optionally determining one or more subsequent QT interval of the patient between one or more of the subsequent IV or oral doses; (G) optionally administering one or more subsequent oral doses to the patient every 12 to 48 hours, wherein the oral dose administered is 125 µg for a patient with a creatinine clearance of 20 to <40 mL/min or 250 µg for a creatinine clearance of 40 to 60 mL/min; and (H) optionally alternatively or in addition wherein the amount of the IV loading dose is in the range of about ±50% of one or more of the subsequent IV or oral doses.

Aspect 27 is a method of initiating or escalating anti-arrhythmic or dofetilide treatment in a patient having atrial fibrillation (AF), atrial flutter (AFL) or both comprising: determining a creatinine clearance of the patient; intravenously administering an anti-arrhythmic or dofetilide according to a dosing regimen, wherein the dosing regimen is chosen from: (a) an IV loading dose of the anti-arrhythmic or dofetilide based on an oral target of 500 µg and one or more subsequent IV doses of the anti-arrhythmic or dofetilide, wherein the IV loading dose and the one or more subsequent IV doses are selected from an amount ranging from 1.6-3 µg/kg; (b) an IV loading dose of the anti-arrhythmic or dofetilide based on an oral target of 250 µg and one or more subsequent IV doses of the anti-arrhythmic or dofetilide, wherein the IV loading dose and the one or more subsequent IV doses are selected from an amount ranging from 0.8-1.6 µg/kg; or (c) an IV loading dose of the anti-arrhythmic or dofetilide based on an oral target of 125 µg and one or more subsequent IV doses of the anti-arrhythmic or dofetilide, wherein the IV loading dose and the one or more subsequent IV doses are selected from an amount ranging from 0.1-0.8 µg/kg; wherein the dosing regimen is chosen based on the creatinine clearance of the patient, such that dosing regimen (a) is chosen for a creatinine clearance of >60 mL/min, dosing regimen (b) is chosen for a creatinine clearance of 40 to 60 mL/min, and dosing regimen (c) is chosen for a creatinine clearance of 20 to <40 mL/min; wherein optionally the IV loading dose is administered over 10, 15, 20, 30, 45, or 60 minutes, optionally by way of several IV doses; wherein optionally one or more of the subsequent IV doses is administered by way of an infusion given over a time period of at least 1 hour; and optionally alternatively or in addition wherein the amount of the IV loading dose and/or one or more of the subsequent IV doses is in the range of about ±50% of the target oral dose.

Aspect 28 is a method of initiating or escalating an anti-arrhythmic or dofetilide treatment in a patient having atrial fibrillation or atrial flutter, comprising: (A) determining a creatinine clearance of the patient; (B) determining a QT interval of the patient; (C) administering to the patient an IV loading dose of an anti-arrhythmic or dofetilide, wherein the IV loading dose is chosen from an amount ranging from: i. 1.6-3 µg/kg, wherein the creatinine clearance of the patient is >60 mL/min; ii. 0.8-1.6 µg/kg, wherein the creatinine clearance of the patient is 40 to 60 mL/min; or iii. 0.1-0.8 µg/kg, wherein the creatinine clearance of the patient is 20 to <40 mL/min; (D) determining a second QT interval of the patient; (E) administering one or more oral doses of the anti-arrhythmic or dofetilide to the patient beginning during the administering of the IV loading dose or immediately, 1-6 hours, or 2-6 hours after completion of the administering of the IV loading dose; (F) optionally determining one or more subsequent QT interval of the patient between one or more of the subsequent oral doses; and (G) optionally alternatively or in addition wherein the amount of the IV loading dose is in the range of about ±50% of one or more of the oral doses.

Aspect 29 is a method of initiating or escalating an anti-arrhythmic or dofetilide treatment in a patient having atrial fibrillation or atrial flutter, comprising: (A) determining a QT interval of a patient with atrial fibrillation or atrial flutter; (B) determining the patient has a creatinine clearance in the range of 20 to 60 mL/min; (C) administering to the patient an IV loading dose of an anti-arrhythmic or dofetilide selected from an amount ranging from 0.1-1.6 µg/kg and optionally administered over a period of from 5 min. to 1 hour; (D) determining a second QT interval of the patient; (E) administering to the patient one or more subsequent IV or oral doses of the anti-arrhythmic or dofetilide beginning immediately, 1-6 hrs, 2-6 hrs, or 2-4 hrs after completion of the IV loading dose; (F) wherein the subsequent IV doses are selected from an amount ranging from 0.1-1.6 µg/kg and optionally administered over a period of from 5 min. to 1 hour; (G) wherein the subsequent oral doses are selected from an amount ranging from 125-250 µg, optionally administered every 12-48 hours; (H) optionally determining one or more subsequent QT interval of the patient between one or more of the subsequent IV and/or oral doses; and (I) optionally alternatively or in addition wherein the amount of the IV loading dose is in the range of about ±50% of one or more of the subsequent IV or oral doses.

Aspect 30 is a method of initiating or escalating an anti-arrhythmic or dofetilide treatment in a patient having atrial fibrillation or atrial flutter, comprising: (A) determining a creatinine clearance of the patient; (B) determining a QT interval of the patient; (C) administering to the patient an IV loading dose of an anti-arrhythmic or dofetilide selected from an amount ranging from: i. 1.6-3 µg/kg, wherein the creatinine clearance of the patient is >60 mL/min; ii. 0.8-1.6 µg/kg, wherein the creatinine clearance of the patient is 40 to 60 mL/min; or iii. 0.1-0.8 µg/kg, wherein the creatinine clearance of the patient is 20 to <40 mL/min; and (D) administering a first oral dose of the anti-arrhythmic or dofetilide to the patient before, during, or upon completion of the IV loading dose, wherein the oral dose is chosen from: i. 500 µg, wherein the creatinine clearance of the patient is >60 mL/min; ii. 250 µg, wherein the creatinine clearance of the patient is 40 to 60 mL/min; or iii. 125 µg, wherein the creatinine clearance of the patient is 20 to <40 mL/min; (E) determining a second QT interval of the patient; (F) administering one or more subsequent oral dose of the anti-arrhythmic or dofetilide to the patient every 12-48 hours; (G) optionally determining one or more subsequent QT interval of the patient between one or more of the subsequent oral doses; (H) optionally alternatively or in addition wherein the amount of the IV loading dose is in the range of about ±50% of the first oral dose and/or one or more of the subsequent oral doses.

Aspect 31 is a method of initiating or escalating anti-arrhythmic or dofetilide treatment in a patient having atrial fibrillation or atrial flutter, comprising: (A) determining a creatinine clearance of the patient; (B) determining a QT interval of the patient; (C) administering to the patient an IV loading dose of an anti-arrhythmic or dofetilide, wherein the IV loading dose is selected from an amount ranging from 0.1 to 3 µg/kg; and (D) administering a first oral dose of the anti-arrhythmic or dofetilide to the patient before, during, or upon completion of the IV loading dose, wherein the oral dose is chosen from: i. 500 µg, wherein the creatinine clearance of the patient is >60 mL/min; ii. 250 µg, wherein the creatinine clearance of the patient is 40 to 60 mL/min; or iii. 125 µg, wherein the creatinine clearance of the patient is 20 to <40 mL/min; (E) determining a second QT interval of the patient; (F) administering one or more subsequent oral dose to the patient every 12-48 hours; (G) optionally determining one or more subsequent QT interval of the patient between one or more of the subsequent oral doses; (H) optionally alternatively or in addition wherein the amount of the IV loading dose is in the range of about ±50% of the first oral dose and/or one or more of the subsequent oral doses.

Aspect 32 is a method of initiating or escalating anti-arrhythmic or dofetilide treatment in a patient having atrial fibrillation or atrial flutter, comprising: (A) determining a creatinine clearance of the patient; (B) determining a QT interval of the patient; (C) administering to the patient an IV loading dose of an anti-arrhythmic or dofetilide, wherein the IV loading dose is selected from an amount ranging from: i. 1.6-3 µg/kg, wherein the creatinine clearance of the patient is >60 mL/min; ii. 0.8-1.6 µg/kg, wherein the creatinine clearance of the patient is 40 to 60 mL/min; or iii. 0.1-0.8 µg/kg, wherein the creatinine clearance of the patient is 20 to <40 mL/min; and (D) administering a first oral dose of the anti-arrhythmic or dofetilide to the patient before, during, or upon completion of the IV loading dose, wherein the first oral dose is selected from 125 µg, 250 µg, or 500 µg; (E) determining a second QT interval of the patient; (F) administering one or more subsequent oral dose of the anti-arrhythmic or dofetilide to the patient every 12-48 hours; and (G) optionally determining one or more subsequent QT interval of the patient between one or more of the subsequent oral doses; (H) optionally alternatively or in addition wherein the amount of the IV loading dose is in the range of about ±50% of the first oral dose and/or one or more of the subsequent oral doses.

Aspect 33 is a method of initiating or escalating an anti-arrhythmic or dofetilide treatment in a patient having atrial fibrillation or atrial flutter, comprising: (A) determining a creatinine clearance of the patient; (B) determining a QT interval of the patient; (C) administering to the patient an IV loading dose of the anti-arrhythmic or dofetilide, wherein the IV loading dose is selected from an amount ranging from 0.1 to 3 µg/kg; (D) administering a first oral dose of the anti-arrhythmic or dofetilide to the patient before, during, or upon completion of the IV loading dose, wherein the first oral dose is chosen from 125 µg, 250 µg, or 500 µg; (E) determining a second QT interval of the patient; (F) administering one or more subsequent oral dose of the anti-arrhythmic or dofetilide to the patient every 12-48 hours, wherein one or more of the subsequent oral doses is a higher dose or a lower dose than the first oral dose; and (G) optionally determining one or more subsequent QT interval of the patient between one or more of the subsequent oral doses; (H) optionally alternatively or in addition wherein the amount of the IV loading dose is in the range of about ±50% of the first oral dose and/or one or more of the subsequent oral doses.

Aspect 34 is a method of initiating or escalating anti-arrhythmic or dofetilide treatment in a patient having atrial fibrillation or atrial flutter, comprising: (A) determining a creatinine clearance of the patient; (B) determining a first QT interval of the patient; (C) administering to the patient an IV loading dose of the anti-arrhythmic or dofetilide, wherein the IV loading dose is selected from an amount ranging from 0.1 to 3 µg/kg; (D) administering a first oral dose of the anti-arrhythmic or dofetilide to the patient before, during, or upon completion of the IV loading dose, wherein the first oral dose is chosen from 125 µg, 250 µg, or 500 µg; (E) determining a second QT interval of the patient that is longer than the first QT interval of the patient; (F) administering one or more subsequent oral dose of the anti-arrhythmic or dofetilide to the patient every 12-48 hours, wherein the one or more subsequent oral dose is a higher dose than the first oral dose to further increase the second QT interval; and (G) optionally determining one or more subsequent QT interval of the patient between one or more of the subsequent oral doses; (H) optionally alternatively or in addition wherein the amount of the IV loading dose is in the range of about ±50% of the first oral dose and/or one or more of the subsequent oral doses.

Aspect 35 is a method of initiating or escalating anti-arrhythmic or dofetilide treatment in a patient having atrial fibrillation or atrial flutter, comprising: (A) determining a creatinine clearance of the patient; (B) determining a first QT interval of the patient; (C) administering to the patient an IV loading dose of the anti-arrhythmic or dofetilide, wherein the IV loading dose is selected from an amount ranging from 0.1 to 3 µg/kg; (D) administering a first oral dose of the anti-arrhythmic or dofetilide to the patient before, during, or upon completion of the IV loading dose, wherein the first oral dose is chosen from 125 µg, 250 µg, or 500 µg; (E) determining a second QT interval of the patient that is longer than the first QT interval of the patient; (F) administering one or more subsequent oral dose of the anti-arrhythmic or dofetilide to the patient every 12-48 hours, wherein the one or more subsequent oral dose is a lower dose than the first oral dose to reduce the QT interval; (G) optionally determining one or more subsequent QT interval of the patient between one or more of the subsequent oral doses; and (H) optionally alternatively or in addition wherein the amount of the IV loading dose is in the range of about ±50% of the first oral dose and/or one or more of the subsequent oral doses.

Aspect 36 is the method of any of Aspects 1-35, wherein the anti-arrhythmic or dofetilide, and/or the IV loading dose, and/or one or more subsequent IV doses, and/or one or more of the IV maintenance doses is administered over 5, 10, 15, 20, 30, 45, or 60 minutes, is administered for up to 60 minutes, is administered over a time period of at least 1 hour, is administered over 0.5, 1, 2, 3, 4, 5, or 6 hours, or is administered for a duration of at least 1 hour, and/or optionally is administered by way of several IV doses.

Aspect 37 is the method of any of Aspects 1-36, wherein the anti-arrhythmic or dofetilide, and/or the IV loading dose, and/or one or more subsequent IV doses, and/or one or more of the IV maintenance doses is administered to a patient who is unable to take (NPO) oral anti-arrhythmics or dofetilide.

Aspect 38 is the method of any of Aspects 1-37, wherein the anti-arrhythmic is one or more of the following drugs: sotalol, amiodarone, ibutilide, dronedarone, procainamide, flecainide, or propafenone, optionally wherein the dosing is adjusted for pharmacokinetics of the drug being administered.

Aspect 39 is a method, comprising: administering an antiarrhythmic, such as dofetilide, to a subject; wherein the subject is a subject with atrial fibrillation cardioverted to normal sinus rhythm, without ventricular arrhythmias or various forms of blocks, and with normal kidney function; and wherein the antiarrhythmic or dofetilide is administered intravenously as a loading dose over a duration of at least 1 hour and in an amount effective for maintenance of normal sinus rhythm.

Aspect 40 is the method of Aspect 39, wherein the amount of the loading dose for dofetilide ranges from 0.1 to 12 µg/kg bodyweight of the subject.

Aspect 41 is the method of Aspect 39 or 40, wherein the amount of the intravenous loading dose for dofetilide is less than 1.8 µg/kg or greater than 3 µg/kg.

Aspect 42 is the method of any of Aspects 39-41, further comprising administering at least one maintenance dose of intravenous and/or oral dofetilide, and optionally alternatively or in addition wherein the amount of the loading dose is in the range of about ±50% of the IV or oral maintenance dose.

Aspect 43 is the method of Aspect 42, wherein the oral dofetilide maintenance dose is in an amount ranging from 125 to 500 µg.

Aspect 44 is the method of Aspect 42 or 43, wherein the intravenous dofetilide maintenance dose is in an amount ranging from 0.1 to 12 µg/kg bodyweight of the subject, such as up to or less than 1.8 µg/kg, such as at least or greater than 3 µg/kg, such as from above 0 up to 1.8 µg/kg, such as from above 0 up to 3 µg/kg, or from 1.8 µg/kg to 3 µg/kg.

Aspect 45 is the method of any of Aspects 42-44, wherein the maintenance oral or IV dofetilide dose(s) is/are administered at an interval of 12-72 hrs.

Aspect 46 is the method of any of Aspects 42-45, wherein the maintenance oral or IV dofetilide dose(s) is/are administered immediately following the IV loading dose, or 0.5 hours after, up to 1 hour after, from 1-6 hours after, from 2-6 hours after, from 2-3 hours after, from 2-4 hours after, from 2-5 hours after, or from 2-12 hours after the IV loading dose.

Aspect 47 is the method of any of Aspects 42-46, wherein the IV maintenance dose is administered for a duration ranging from up to or including any one or more of 5 hours, 4 hours, 3 hours, 2 hours, 1 hour, 45 min., 30 min., 15 min., 10 min., or 5 min.

Aspect 48 is the method of any of Aspects 39-47, wherein the subject is a subject who is unable (NPO) to take oral dofetilide.

Aspect 49 is a method, comprising: administering an antiarrhythmic, such as dofetilide, to a subject; wherein the subject is a subject with atrial fibrillation cardioverted to normal sinus rhythm, without ventricular arrhythmias or various forms of blocks, and with reduced kidney function; and wherein the antiarrhythmic or dofetilide is administered intravenously as a loading dose over a duration of at least 1 hour and in an amount effective for maintenance of normal sinus rhythm.

Aspect 50 is the method of Aspect 49, wherein the subject has a creatinine clearance of 20 mL/min to 40 mL/min.

Aspect 51 is the method of Aspect 49, wherein the subject has a creatinine clearance of 40 mL/min to 60 mL/min.

Aspect 52 is the method of Aspect 49, wherein the subject has a creatinine clearance of 60 mL/min to 90 mL/min.

Aspect 53 is the method of any of Aspects 49-52, wherein the amount of the loading dose for dofetilide ranges from 0.1 to 12 µg/kg bodyweight of the subject.

Aspect 54 is the method of any of Aspects 49-52, wherein the amount of the intravenous loading dose for dofetilide is less than 1.8 µg/kg or greater than 3 µg/kg.

Aspect 55 is the method of any of Aspects 49-54, further comprising administering at least one maintenance dose of intravenous and/or oral dofetilide, and optionally alternatively or in addition wherein the amount of the loading dose is in the range of about ±50% of one or more of the maintenances doses.

Aspect 56 is the method of Aspect 55, wherein the maintenance dose is one or more oral dofetilide maintenance dose and is in an amount ranging from 125 to 500 µg, and optionally alternatively or in addition wherein the amount of the loading dose is in the range of about ±50% of one or more of the oral dofetilide maintenances doses.

Aspect 57 is the method of Aspect 55 or 56, wherein the intravenous dofetilide maintenance dose is in an amount ranging from 0.1 to 12 µg/kg bodyweight of the subject, such as up to or less than 1.8 µg/kg, such as at least or greater than 3 µg/kg, such as from above 0 up to 1.8 µg/kg, such as from above 0 up to 3 µg/kg, or from 1.8 µg/kg to 3 µg/kg.

Aspect 58 is the method of any of Aspects 55-57, wherein the maintenance oral or IV dofetilide dose(s) is/are administered at an interval of 12-72 hrs.

Aspect 59 is the method of any of Aspects 55-58, wherein the maintenance oral or IV dofetilide dose(s) is/are administered immediately following the IV loading dose, or 0.5 hours after, up to 1 hour after, from 1-6 hours after, from 2-6 hours after, from 2-3 hours after, from 2-4 hours after, from 2-5 hours after, or from 2-12 hours after the IV loading dose.

Aspect 60 is the method of any of Aspects 55-59, wherein the IV maintenance dose is administered for a duration ranging from up to or including any one or more of 5 hours, 4 hours, 3 hours, 2 hours, 1 hour, 45 min., 30 min., 15 min., 10 min., or 5 min.

Aspect 61 is the method of any of Aspects 49-60, wherein the subject is a subject who is unable (NPO) to take oral dofetilide.

Aspect 62 is a method of initiating dofetilide treatment, comprising: a. determining a QTc of a patient; b. administering a loading dose of dofetilide intravenously to the patient; c. determining a second QTc of the patient; d. administering a first maintenance dose of dofetilide orally or intravenously to the patient; and e. optionally administering one or more subsequent maintenance dose of dofetilide orally or intravenously to the patient.

Aspect 63 is the method of any of Aspects 1-62, wherein the loading dose is divided into multiple intravenous doses optionally administered to the patient with a delay between each dose.

Aspect 64 is the method of any of Aspects 1-63, wherein the loading dose is selected from an amount in the range of about ±50% of the amount of the oral dose.

Aspect 65 is the method of any of Aspects 1-64, wherein the loading dose is selected from an amount in the range of about ±25% of the amount of the oral dose.

Aspect 66 is the method of any of Aspects 1-65, wherein the loading dose is selected from an amount in the range of about ±50% of the amount of the maintenance dose.

Aspect 67 is the method of any of Aspects 1-66, wherein the loading dose is selected from an amount in the range of about ±25% of the amount of the maintenance dose.

According to some more specific implementations, the anti-arrhythmic or dofetilide can be administered intravenously as a loading dose in the range of above 0 µg/kg up to 8 µg/kg, including 0.1, 0.2, 0.3, 0.4, 0.5, 0.6, 0.7, 0.8, 0.9, 1.0, 1.2, 1.4, 1.5, 1.6, 1.8, 2.0, 2.2, 2.4, 2.5, 2.6, 2.8, 3.0, 3.2, 3.4, 3.5, 3.6, 3.8, 4.0, 4.2, 4.4, 4.5, 4.6, 4.8, 5.0, 5.2, 5.4, 5.5, 5.6, 5.8, 6.0, 6.2, 6.4, 6.5, 6.6, 6.8, 7.0, 7.2, 7.4, 7.5, 7.6, 7.8, 8.0, µg/kg, or in any range with any of these values as lower or upper values, such as 1.5 to 4.4 µg/kg, 3.2 to 6.8 µg/kg, 2.6 to 5.4 µg/kg, 2.0 to 6.0 µg/kg, 1.8 to 4.8 µg/kg, and so on. Depending on the particular anti-arrhythmic selected (such as for sotalol, amiodarone, ibutilide, dronedarone, procainamide, flecainide, or propafenone), the dosing can be adjusted up or down to be commensurate with the pharmacokinetics of the drug being administered. Higher loading doses, such as those exceeding 8.0 µg/kg, such as 8.2 to 12.0 µg/kg, including 8.2, 8.4, 8.5, 8.6, 8.8, 9.0, 9.2, 9.4, 9.5, 9.6, 9.8, 10.0, 10.2, 10.4, 10.5, 10.6, 10.8, 11.0, 11.2, 11.4, 11.5, 11.6, 11.8, and 12.0 µg/kg, or in any range with any of these values as lower and upper values, such as 8.2 to 10 µg/kg may be possible, such as, if administered over longer durations. The loading dose can be slowly titrated upward until restoration of normal sinus rhythm as measured by electrocardiogram (ECG), or ceased or adjusted downward if ventricular arrhythmias, ventricular tachycardia, or other side effects of dofetilide such as dizziness are observed. The loading dose can be adjusted for patient QTc as described below. The loading dose can be adjusted for patient creatinine clearance as described below. The loading dose can be administered over 0.5 to 60 minutes or longer, including for 0.5, 1, 2, 3, 4, 5, 6, 7, 8, 9, 10, 11, 12, 13, 14, 15, 20, 25, 30, 35, 40, 45, 50, 55, or 60 minutes, or within any range with any of these values as lower and upper values, such as 5 to 20 minutes, 10 to 40 minutes, 15 to 30 minutes, 20 to 45 minutes, 30 to 60 minutes, 35 to 50 minutes, 35 to 60 minutes, 40 to 60 minutes, 45 to 60 minutes, and so on. Similar to the changes made in dose for a particular anti-arrhythmic being used, depending on the particular anti-arrhythmic selected (such as for sotalol, amiodarone, ibutilide, dronedarone, procainamide, flecainide, or propafenone), the duration of the IV administration can be adjusted up or down to be commensurate with the pharmacokinetics of the drug being administered. The loading dose can be intravenously infused into a central or peripheral vein of the patient. The flow rate of the intravenous dose can be adjusted based on the concentration of the anti-arrhythmic or dofetilide in the intravenous formulation, the desired duration of administration, and the body weight of the patient to achieve a specific loading dose in µg/kg or mg/kg, if appropriate for the particular anti-arrhythmic being used. Thus, longer administration durations of a specific dose (X µg/kg or mg/kg) will typically have slower flow rates compared to shorter administration durations to achieve the same dose. In embodiments, the intravenous loading dose amount is selected from an amount in the range of about ±50% of an oral dose or maintenance dose, such as an amount of up to about ±5%, ±10%, ±15%, ±20%, ±25%, ±30%, ±35%, ±40%, or ±45%, or any range in between.

According to some implementations, after the loading dose, the anti-arrhythmic or dofetilide can be infused intravenously as a maintenance dose rate in the range of above 0 µg/kg/hr up to 10 µg/kg/hr, including 0.1, 0.2, 0.3, 0.4, 0.5, 0.6, 0.7, 0.8, 0.9, 1.0, 1.2, 1.3, 1.4, 1.5, 1.6, 1.8, 1.9, 2.0, 2.2, 2.4, 2.5, 2.6, 2.7, 2.8, 3.0, 3.1, 3.2, 3.3, 3.4, 3.5, 3.6, 3.8, 4.0, 4.2, 4.3, 4.4, 4.5, 4.6, 4.7, 4.8, 5.0, 5.1, 5.2, 5.4, 5.5, 5.6, 5.7, 5.8, 6.0, 6.1, 6.2, 6.4, 6.5, 6.6, 6.8, 6.9, 7.0, 7.2, 7.4, 7.5, 7.6, 7.7, 7.8, 7.9, 8.0, 8.1, 8.2, 8.3, 8.4, 8.5, 8.6, 8.8, 8.9, 9.0, 9.2, 9.4, 9.5, 9.6, 9.7, 9.8, 9.9, 10.0 µg/kg/hr, or in any range with any of these values as lower or upper values, such as 1.2 to 2.8 µg/kg/hr, 2.6 to 7.4 µg/kg/hr, 3.4 to 5.8 µg/kg/hr, 4.2 to 8.6 µg/kg/hr, 1.0 to 3.0 µg/kg/hr, 2.8 to 3.6 µg/kg/hr, 1.0 to 4 µg/kg/hr, 1.2 to 4 µg/kg/hr, 1.4 to 4 µg/kg/hr, 1.6 to 4 µg/kg/hr, 1.8 to 4 µg/kg/hr, 2.0 to 4 µg/kg/hr, 2.2 to 4 µg/kg/hr, 2.4 to 4 µg/kg/hr, 2.6 to 4 µg/kg/hr, 2.7 to 4 µg/kg/hr, 2.8 to 4 µg/kg/hr, 1.0 to 5 µg/kg/hr, 1.2 to 5 µg/kg/hr, 1.4 to 5 µg/kg/hr, 1.6 to 5 µg/kg/hr, 1.8 to 5 µg/kg/hr, 2.0 to 5 µg/kg/hr, 2.2 to 5 µg/kg/hr, 2.4 to 5 µg/kg/hr, 2.6 to 5 µg/kg/hr, 2.7 to 5 µg/kg/hr, 2.8 to 5 µg/kg/hr, 3.0 to 5 µg/kg/hr, 3.2 to 5 µg/kg/hr, 3.4 to 5 µg/kg/hr, 3.6 to 5 µg/kg/hr, 1.0 to 6 µg/kg/hr, 1.2 to 6 µg/kg/hr, 1.4 to 6 µg/kg/hr, 1.6 to 6 µg/kg/hr, 1.8 to 6 µg/kg/hr, 2.0 to 6 µg/kg/hr, 2.2 to 6 µg/kg/hr, 2.4 to 6 µg/kg/hr, 2.6 to 6 µg/kg/hr, 2.7 to 6 µg/kg/hr, 2.8 to 6 µg/kg/hr, 3.0 to 6 µg/kg/hr, 3.2 to 6 µg/kg/hr, 3.2 to 6 µg/kg/hr, 3.4 to 6 µg/kg/hr, 3.6 to 6 µg/kg/hr, 3.8 to 6 µg/kg/hr, 4.0 to 6 µg/kg/hr, 1.0 to 8 µg/kg/hr, 1.2 to 8 µg/kg/hr, 1.4 to 8 µg/kg/hr, 1.6 to 8 µg/kg/hr, 1.8 to 8 µg/kg/hr, 2.0 to 8 µg/kg/hr, 2.2 to 8 µg/kg/hr, 2.4 to 8 µg/kg/hr, 2.6 to 8 µg/kg/hr, 2.7 to 8 µg/kg/hr, 2.8 to 8 µg/kg/hr, 3.0 to 8 µg/kg/hr, 3.2 to 8 µg/kg/hr, 3.4 to 8 µg/kg/hr, 3.6 to 8 µg/kg/hr, 3.8 to 8 µg/kg/hr, 4.0 to 8 µg/kg/hr, 4.2 to 8 µg/kg/hr, 4.4 to 8 µg/kg/hr, 4.6 to 8 µg/kg/hr, 4.8 to 8 µg/kg/hr, 5.0 to 8 µg/kg/hr, 1.0 to 10 µg/kg/hr, 1.2 to 10 µg/kg/hr, 1.4 to 10 µg/kg/hr, 1.6 to 10 µg/kg/hr, 1.8 to 10 µg/kg/hr, 2.0 to 10 µg/kg/hr, 2.2 to 10 µg/kg/hr, 2.4 to 10 µg/kg/hr, 2.6 to 10 µg/kg/hr, 2.7 to 10 µg/kg/hr, 2.8 to 10 µg/kg/hr, 3.0 to 10 µg/kg/hr, 3.2 to 10 µg/kg/hr, 3.4 to 10 µg/kg/hr, 3.6 to 10 µg/kg/hr, 3.8 to 10 µg/kg/hr, 4.0 to 10 µg/kg/hr, 4.2 to 10 µg/kg/hr, 4.4 to 10 µg/kg/hr, 4.6 to 10 µg/kg/hr, 4.8 to 10 µg/kg/hr, and 5.0 to 10 µg/kg/hr 5.2 to 10 µg/kg/hr, 5.4 to 10 µg/kg/hr, 5.6 to 10 µg/kg/hr, 5.8 to 10 µg/kg/hr, 6.0 to 10 µg/kg/hr, and so on.

Depending on the particular anti-arrhythmic selected (such as for sotalol, amiodarone, ibutilide, dronedarone, procainamide, flecainide, or propafenone), the IV maintenance dose can be adjusted up or down to be commensurate with the pharmacokinetics of the drug being administered. In embodiments, the maintenance dose is initiated at a higher rate and then titrated down. In other embodiments, the maintenance dose is initiated at a lower rate and then increased.

The maintenance dose (IV or oral) can be administered over a duration of 30 minutes to several hours to several days to several months to several years, including 0.5, 1.0, 1.5, 2.0, 2.5, 3.0, 3.5, 4.0, 4.5, 5.0, 5.5, 6.0, 6.5, 7.0, 7.5, 8.0, 9, 10, 11, 12, 13, 14, 15, 16, 17, 18, 19, 20, 21, 22, 23, 24, 36, 48, 72 hours, including 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days, or including 1, 2, 3, 4, 5, 6, 7, 8, 9, 10, 11, 12 months, or including 1, 2, 3, 4, 5, 8, or 10 years, or in any range with any of these values as lower and upper values, such as 0.5 to 1.5 hours, 1 to 2 hours, 1 to 3 hours, 1 to 4 hours, 1 to 5 hours, 1 to 6 hours, 1 to 10 hours, 1 to 18 hours, 1 to 24 hours, 1 to 36 hours, 1 to 48 hours, 1 to 72 hours, 1 to 168 hours, 2 to 3 hours, 2 to 4 hours, 2 to 5 hours, 2 to 6 hours, 2 to 8 hours, 2 to 10 hours, 2 to 18 hours, 2 to 24 hours, 2 to 36 hours, 2 to 48 hours, 2 to 72 hours, 2 to 168 hours, 3 to 4 hours, 3 to 5 hours, 3 to 6 hours, 3 to 10 hours, 3 to 18 hours, 3 to 24 hours, 3 to 36 hours, 3 to 48 hours, 3 to 72 hours, 3 to 168 hours, 4 to 8 hours, 4 to 10 hours, 4 to 18 hours, 4 to 24 hours, 4 to 36 hours, 4 to 48 hours, 4 to 72 hours, 4 to 168 hours, 6 to 8 hours, 6 to 10 hours, 6 to 18 hours, 6 to 24 hours, 6 to 36 hours, 6 to 48 hours, 6 to 72 hours, 6 to 168 hours, 8 to 10 hours, 8 to 18 hours, 8 to 24 hours, 8 to 36 hours, 8 to 48 hours, 8 to 72 hours, 8 to 168 hours, 12 to 24 hours, 12 to 72 hours, 12 to 168 hours, 24 to 72 hours, 1 to 7 days, 1 to 10 days, 1 to 14 days, 7 to 30 days, 1 to 3 months, 2 to 6 months, 1 to 5 years, and so on.

The maintenance dose can be initiated immediately after completion of the loading dose, or can be initiated after a delay of 0.5 hours to 6 hours, such as a delay of from 1, 1.5, 2, 2.5, 3, 3.5, 4, 4.5, 5, or 5.5 hours after completion of the loading dose.

The maintenance dose can be intravenously infused into a central or peripheral vein of the patient. In other embodiments, the maintenance dose can be given orally. In an embodiment, the maintenance dose is initiated as an IV infusion, then transitioned to oral administration. The patient can be monitored by electrocardiogram (ECG) for normal sinus rhythm and/or ventricular arrhythmias or ventricular tachycardia and the maintenance dose rate adjusted upward until normal sinus rhythm is reached or adjusted downward if ventricular arrhythmias, ventricular tachycardia, or other side effects typically associated with anti-arrhythmic or dofetilide administration, such as dizziness occur. The maintenance dose can be adjusted for patient QTc as described below. The maintenance dose rate can be adjusted for patient creatinine clearance as described below. The flow rate of the intravenous dose can be adjusted based on the concentration of dofetilide in the intravenous formulation and the body weight of the patient to achieve a specific maintenance dose rate in µg/kg/hr. The maintenance dose rate can be targeted to reach a particular therapeutic, steady-state plasma concentration based on established pharmacokinetic parameters of dofetilide such as half-life and clearance. As can be appreciated, the cumulative maintenance dose is a product of the rate of intravenous infusion in µg/kg/hr multiplied by the infusion duration in hours.

QT Interval Monitoring

Proper dosing for any of dofetilide, sotalol, amiodarone, ibutilide, dronedarone, procainamide, flecainide, or propafenone can be ascertained by monitoring the QT interval, or the heart rate corrected QT (the QTc), during or after IV infusion of the loading and/or maintenance dose(s), and thus avoid the development of life-threatening ventricular tachycardias such as Torsades de Pointes. Patients can be monitored by electrocardiogram (ECG) and a baseline QTc can be measured. A baseline QTc exceeding a certain threshold, such as 440 msec, may exclude some patients from dofetilide treatment (see US Patent Application Publication No. 20190388371A1). For patients that qualify for treatment, the QTc can be monitored during infusion of the loading and/or maintenance dose, and such dose can be adjusted downward or ceased if the patient's QTc becomes too high, either over a QTc threshold or a change exceeding a patient's baseline QTc. In one implementation, the QTc threshold is 500 msec. In various implementations, the change exceeding baseline QTc can be 5, 10, 15, or 20% over baseline QTc. The QTc can be measured at regular intervals, such as every 10, 15, 20, 30, 45, or 60 minutes during treatment. In some situations, such as if the patient's heart rate is less than 60 bpm, the uncorrected QT interval can be used. Remote ECG monitoring, such as Holter monitoring or event monitoring, may be indicated for long term monitoring of QT or QTc.

Creatinine Clearance

Because elimination of dofetilide is primarily renal, renal impairment can potentially lead to toxic serum concentrations. As such, it is desirable to measure patient creatinine clearance prior to initiating a dofetilide dosing regimen in order to gauge kidney function. Serum samples can be taken from the patient prior to treatment with dofetilide and serum creatinine measured according the following formulas:

Creatinine clearance (male)=[(140−Age)×Body Wt (kg)]/[72×serum creatinine (mg/dL)]

Creatinine clearance (female)=Creatine clearance (male)×0.85

The loading dose and maintenance dose can be adjusted according to creatinine clearance as provided in Table I.

TABLE I

| Creatinine Clearance (mL/min) | Loading Dose | Maintenance Dose |
| --- | --- | --- |
| >60 | High | High |
| 40-60 | Medium | Medium |
| 20-40 | Low | Low |
| <20 | Dofetilide not indicated | Dofetilide not indicated |

Indications

Dofetilide administered intravenously in any of the above loading and/or maintenance doses and durations can be used to treat or prevent such conditions as atrial fibrillation or flutter (sustained or intermittent), paroxysmal atrial fibrillation, ventricular tachycardia, ventricular fibrillation, paroxysmal supraventricular tachycardia, heart failure, coronary artery disease, pulmonary artery hypertension, and the like, and for situations where the patient is unable to take an anti-arrhythmic by mouth (NPO). Other anti-arrhythmics can be substituted for dofetilide, including other Class III anti-arrhythmics such as sotalol, amiodarone, ibutilide, and dronedarone or Class I anti-arrhythmics such as procainamide, flecainide, and propafenone. Adjustments to the dosing for a particular substitute can be made by one of ordinary skill in the art based on dosages appropriate for a particular drug. For example, similar dosages can be used for ibutilide, while for amiodarone, dronedarone, propafenone, procainamide, flecainide and sotalol, the dosing would be on the order of mg/kg instead of the µg/kg indicated for dofetilide. For some drugs the oral maintenance dose may be lower or higher than a corresponding dose for dofetilide and/or may be administered more frequently or less frequently than dofetilide. The specific intravenous loading dose and intravenous maintenance dose rate protocols would be selected from those described herein based upon the patient's condition, baseline and in-treatment QTc, as well as the patient's creatinine clearance. Other factors affecting selection of the loading and maintenance dose include patient body weight. In cases where there is no intravenous maintenance dose rate protocol (i.e. "none"), an oral maintenance dose of dofetilide can be administered to the patient according to available oral dosages (125 µg, 250 µg, 500 µg, typically given twice daily), QTc, creatinine clearance, body weight, and other factors, as described by U.S. Patent Application Publication No. 20190388371A1). Situations where IV loading and/or maintenance doses are appropriate include those in which the patient cannot take oral administration (NPO), or for gastrointestinal conditions resulting in poor absorption, recovery from GI surgery, and/or intensive care.

Dofetilide administration according to embodiments of the invention is administered to patients naïve to dofetilide treatment and/or to patients currently receiving dofetilide therapy and/or to patients having previously received dofetilide.

In embodiments, the dofetilide dose (including the loading dose and/or maintenance dose, whether IV or oral) is determined by patient characteristics including body weight, sex, and/or creatinine clearance.

In embodiments, antiarrhythmics, such as dofetilide, can be administered to subjects/patients hospitalized with atrial fibrillation cardioverted to normal sinus rhythm, typically without ventricular arrhythmias or various forms of blocks, and typically in patients with normal kidney function. In other embodiments, the patients have reduced kidney function or can have ventricular arrhythmias, blocks or other cardiovascular conditions/diseases.

Atrial fibrillation (AF) is a heart rhythm disorder caused by a degeneration of the electrical impulses of the atria resulting in a rapid, chaotic rhythm (also called an arrhythmia). This arrhythmia is a direct result of disordered impulses across the atrioventricular (AV) node, to the lower cardiac chambers (ventricles). The arrhythmia causes ineffectual atrial contractions, which affect cardiac output and leads to vulnerability to thrombus formation that can result in strokes and related cardiovascular accidents. (See https://www.clevelandclinicmeded.com/medicalpubs/diseasemanagement/cardiology/atrial-fibrillation/, which is hereby incorporated by reference herein in its entirety.)

Unstable patients presenting with AF, such as patients with chest pain, pulmonary edema, or hypotension, are typically treated by rapid electrical cardioversion. Patients thus cardioverted to a normal sinus rhythm can be treated with antiarrhythmic drugs, such as dofetilide, a class III antiarrhythmic indicated for maintenance of normal sinus rhythm in patients with atrial fibrillation of greater than one week duration who have been converted to normal sinus rhythm. (See TIKOSYN package insert, rev. 2014, which is hereby incorporated by reference herein in its entirety.) Treatment with dofetilide is sometimes accompanied by serious side effects. These include ventricular arrhythmias (including ventricular fibrillation, ventricular tachycardia and torsade de Pointes) and various forms of block (AV block, bundle branch block and heart block).

The incidence of these side effects appears related to QT prolongation, which itself is directly related to dofetilide plasma concentration. Clearance of dofetilide decreases with decreasing creatine clearance. Therefore, dosage adjustments are typically based on calculated creatine clearance. Accordingly, one way to obviate these life-threatening side effects is to administer an intravenous formulation of dofetilide only to those patients without ventricular arrhythmias or heart blocks. In embodiments, an intravenous formulation of dofetilide is administered to patients who have normal kidney function. In other embodiments, an intravenous formulation of dofetilide may be administered to patients with reduced kidney function. In embodiments, the patient has a creatinine clearance of about 20 mL/min to about 90 mL/min, such as about 40 mL/min to about 60 mL/min.

Such therapy can account for the black box warning given for TIKOSYN. Initiation of oral dofetilide therapy typically requires that patients be placed for a minimum of three days in a facility that can provide calculated creatinine clearance, continuous ECG monitoring, and cardiac resuscitation. Treatment with the intravenous formulation of dofetilide is expected to shorten this observation period to one day or less. This will result in substantial savings in both time and cost, while providing practitioners with all the necessary information relating to the patient's ability to leave the facility on oral dofetilide or another therapeutic agent.

The following Examples are provided to illustrate various protocols for administering anti-arrhythmics, such as dofetilide. Although dofetilide is primarily exemplified in the Examples, other anti-arrhythmics can be substituted, and depending on the particular anti-arrhythmic selected (such as for sotalol, amiodarone, ibutilide, dronedarone, procainamide, flecainide, or propafenone), the dose and/or rate of administration in any of the Examples can be adjusted up or down to be commensurate with the pharmacokinetics of the particular drug being administered.

Example 1

An example dofetilide or anti-arrhythmic treatment protocol for a patient experiencing a ventricular conduction abnormality, such as atrial flutter, is described herein. The male patient, age 60, is admitted to the hospital to initiate anti-arrhythmic, such as dofetilide, treatment. The patient's creatinine clearance is measured/determined to be >60 mL/min. The patient is connected to an electrocardiograph, and treatment is initiated with an IV loading dose of dofetilide in an amount of up to 3.5 µg/kg infused over up to 1 hour. The patient's QT is measured/determined prior to start of the IV and is monitored every 15 minutes during the IV loading dose administration along with heart rate (HR) and blood pressure (BP). The patient's QTc is calculated from the QT measurement. If the patient's baseline (i.e., prior to dofetilide administration) QT interval or baseline QTc is greater than 500 msec (in patients with ventricular conduction abnormalities), then dofetilide is contraindicated. Measure every 15 min. during the IV loading dose, and if the QT or QTc increases by greater than 20% of the patient's baseline QT or baseline QTc (or is greater than 550 msec), then the IV dofetilide is discontinued or a subsequent lower dose is considered or administered. If after any subsequent IV or oral dose the QT or QTc increases to greater than 550 msec, then dofetilide is discontinued.

Immediately or one hour after completion of the loading dose, the patient receives a maintenance dose of dofetilide delivered by way of a second IV infusion of up to 2.5 µg/kg over 5 hours. The patient's QT or QTc is monitored every hour during the administration of the IV maintenance dose. If during or after the IV maintenance dose the patient's QT or QTc is greater than 550 msec or if the QT or QTc increases by greater than 20% of the patient's baseline QT or QTc, then the IV maintenance dose is reduced and subsequent IV maintenance doses are delivered at approximately 1.25 µg/kg over up to 5 hours.

For the situation where QT or QTc is within an acceptable range, one or more subsequent IV or oral maintenance doses, selected from a 2.5 µg/kg IV infusion over up to 5 hours or a 500 µg oral dose, are repeated every 12 hours until Cmax ss is reached and the patient can be released to continue dofetilide treatment orally outside the hospital. For the situation where (i) the patient's QT or QTc after administration of the first IV maintenance dose is greater than 550 msec, (ii) the patient's subsequent dose is reduced, and (iii) the QT or QTc for the subsequent reduced maintenance dose (or any subsequent maintenance dose) is observed to be greater than 550 msec, additional subsequent maintenance doses can be further reduced to a 0.5-0.9 µg/kg IV infusion over 5 hours, and/or given over a longer infusion time, and/or reduced to a 125 µg oral dose, or dofetilide treatment is discontinued.

Example 2

An example anti-arrhythmic, such as dofetilide, treatment protocol for a patient experiencing a ventricular conduction abnormality, such as atrial flutter, is described herein. The male patient, age 60, is admitted to the hospital to initiate treatment. The patient's creatinine clearance is determined to be between 40 and 60 mL/min. The patient is connected to an electrocardiograph, and an initial (or baseline) QT interval is determined to be not greater than 500 msec. Treatment is initiated with an IV loading dose of up to 1.6 µg/kg infused over up to 1 hour. The loading dose may be administered by way of several smaller IV doses. The patient's QT interval is measured every 15 minutes during the IV loading dose administration along with HR and BP.

During or following administration of the IV loading dose, the patient's QT interval is determined to be greater than 550 msec. A reduced maintenance dose is administered to the patient up to 6 hours after completion of the IV loading dose or dofetilide administration is discontinued. The reduced maintenance dose is administered as an oral dose of 125 µg. The patient's QT interval is monitored following administration of the oral maintenance dose. The patient's QT interval no longer exceeds 550 msec and the ΔQTc is not greater than 20% of the patient's initial QTc. Subsequent oral maintenance doses of 125 µg are given every 12 to 48 hours.

Example 3

An example anti-arrhythmic/dofetilide treatment protocol for a patient experiencing a ventricular conduction abnormality, such as atrial flutter, is described herein. The male patient, age 60, is admitted to the hospital to initiate treatment. The patient's creatinine clearance is determined to be between 20 and 40 mL/min. The patient is connected to an electrocardiograph, and an initial QT interval is determined to be not greater than 500 msec. Treatment is initiated with an IV loading dose of up to 1.6 µg/kg infused over up to 1 hour. The loading dose may be administered by way of several smaller IV doses. The patient's QT interval is measured every 15 minutes during the IV loading dose administration along with HR and BP.

During and following administration of the loading dose, the patient's QT interval is determined to be not greater than 550 msec and ΔQTc is not greater than 20% of the patient's initial QTc. A maintenance dose is administered to the patient up to 6 hours after completion of the IV loading dose. The maintenance dose is administered as an oral dose of 125 µg. The patient's QT interval is monitored following administration of the oral maintenance dose. The patient's QT interval still does not exceed 550 msec and is not greater than 20% of the patient's initial QTc. Subsequent oral maintenance doses of 125 µg are given every 12 to 48 hours.

Example 4

An example anti-arrhythmic/dofetilide treatment protocol for a patient experiencing a ventricular conduction abnormality, such as atrial flutter, is described herein. The male patient, age 60, is admitted to the hospital to initiate treatment. The patient's creatinine clearance is determined to be >60 mL/min. The patient is connected to an electrocardiograph, and an initial QT interval is determined. Treatment is initiated with an IV loading dose based on an oral target dose of 500 which is administered in an amount of up to 3 µg/kg and is infused over up to 1 hour. The patient's QT interval is measured every 15 minutes during the IV loading dose administration along with HR and BP.

During and following administration of the loading dose, the patient's QT interval is determined to be not greater than 550 msec and the ΔQTc is not greater than 20% of the patient's initial QTc. A maintenance dose is administered to the patient as an IV dose of up to 3 µg/kg. The IV maintenance dose is administered over a time period of up to 60 minutes. The patient's QT interval is monitored during and following administration of the IV maintenance dose. The patient's QT interval still does not exceed 550 msec and the ΔQTc is not greater than 20% of the patient's initial QTc. Subsequent oral maintenance doses of 500 µg are given every 12 to 48 hours.

Example 5

An example anti-arrhythmic/dofetilide treatment protocol for a patient experiencing a ventricular conduction abnormality, such as atrial flutter, is described herein. The male patient, age 60, is admitted to the hospital to initiate treatment. The patient's creatinine clearance is determined to be between 40 and 60 mL/min. The patient is connected to an electrocardiograph, and an initial QT interval is determined. Treatment is initiated with an IV loading dose based on an oral target of 250 which is administered in an amount of up to 1.6 µg/kg and is infused over about 1 hour. The patient's QT interval is measured every 15 minutes during the IV loading dose administration along with HR and BP.

During and following administration of the loading dose, the patient's QT interval is determined to be not greater than 550 msec and the ΔQTc is not greater than 20% of the patient's initial QTc. A maintenance dose is administered to the patient as an IV dose of up to 1.6 µg/kg. The IV dose is administered over a time period of up to 60 minutes. The patient's QT interval is monitored during and following administration of the IV maintenance dose. The patient's QT interval still does not exceed 550 msec and the ΔQTc is not greater than 20% of the patient's initial QTc. Subsequent IV maintenance doses of up to 1.6 µg/kg are given every 12 to 48 hours.

Example 6

An example anti-arrhythmic/dofetilide treatment protocol for a patient experiencing a ventricular conduction abnormality, such as atrial flutter, is described herein. The male patient, age 60, is admitted to the hospital to initiate treatment. The patient's creatinine clearance is determined to be between 20 and 40 mL/min. The patient is connected to an electrocardiograph, and an initial QT interval is determined. Treatment is initiated with an IV loading dose based on an oral target of 125 µg, which is administered in an amount of up to 0.8 µg/kg and is infused over about 1 hour. The patient's QT interval is measured every 15 minutes during the IV loading dose administration along with HR and BP.

During and following administration of the IV loading dose, the patient's QT interval is determined to be not greater than 550 msec and the ΔQTc is not greater than 20% of the patient's initial QTc. A maintenance dose is administered to the patient as an IV dose of up to 0.8 µg/kg. The IV maintenance dose is administered over a time period of up to 60 minutes. The patient's QT interval is monitored during and following administration of the IV maintenance dose. The patient's QT interval still does not exceed 550 msec and the ΔQTc is not greater than 20% of the patient's initial QTc. Subsequent IV maintenance doses of up to 0.8 µg/kg are given every 12 to 48 hours.

Example 7

An example anti-arrhythmic/dofetilide treatment protocol for a patient experiencing a ventricular conduction abnormality, such as atrial flutter, is described herein. The female patient, age 60, is admitted to the hospital to initiate treatment. The patient's creatinine clearance is determined to be >60 mL/min. The patient is connected to an electrocardiograph, and an initial QT interval is determined to be in an acceptable range. Treatment is initiated with an IV loading dose in the range of 1.6-3 µg/kg. The patient's QT interval is measured every 15 minutes during the IV loading dose administration along with HR and BP.

During or following administration of the IV loading dose, the patient's QT interval is determined to be not greater than 550 msec, but the ΔQTc is greater than 20% of the patient's initial QTc. A maintenance dose is administered to the patient in a reduced amount as an oral dose of 250 The patient's QT interval is monitored following administration of the first oral maintenance dose. The patient's QT interval still does not exceed 550 msec and the ΔQTc is no longer greater than 20% of the patient's initial QTc. Subsequent oral maintenance doses of 250 µg are given every 12 to 48 hours.

Example 8

An example anti-arrhythmic/dofetilide treatment protocol for a patient experiencing a ventricular conduction abnormality, such as atrial flutter, is described herein. The male patient, age 50, is admitted to the hospital to initiate treatment. The patient's creatinine clearance is determined to be between 40 and 60 mL/min. The patient is connected to an electrocardiograph, and an initial QT interval is determined. Treatment is initiated with an IV loading dose of 0.8-1.6 µg/kg. The patient's QT interval is measured every 15 minutes during the IV loading dose administration along with HR and BP.

During and following administration of the IV loading dose, the patient's QT interval is determined to be not greater than 550 msec and the ΔQTc is not greater than 20% of the patient's initial QTc. A first maintenance dose is administered to the patient as an oral dose of 250 The patient's QT interval is monitored following administration of the first oral maintenance dose. The patient's QT interval is determined to be less than 550 msec and the ΔQTc is not greater than 20% of the patient's initial QTc. Subsequent oral maintenance doses of 250 µg are given every 12 to 48 hours.

Example 9

An example anti-arrhythmic/dofetilide treatment protocol for a patient experiencing a ventricular conduction abnormality, such as atrial flutter, is described herein. The male patient, age 40, is admitted to the hospital to initiate treatment. The patient's creatinine clearance is determined to be between 20 and 40 mL/min. The patient is connected to an electrocardiograph, and an initial QT interval is determined. Treatment is initiated with an IV loading dose of 0.1-0.8 µg/kg. The patient's QT interval is measured every 15 minutes during the IV loading dose administration along with HR and BP.

During and following administration of the IV loading dose, the patient's QT interval is not greater than 550 msec and the ΔQTc is not greater than 20% of the patient's initial QTc. A first maintenance dose is administered to the patient as an oral dose of 125 The patient's QT interval is monitored following administration of the first oral maintenance dose. The patient's QT interval is determined to be less than 550 msec and the ΔQTc is not greater than 20% of the patient's initial QTc. Subsequent oral maintenance doses of 125 µg are given every 12 to 48 hours.

Example 10

An example anti-arrhythmic/dofetilide treatment protocol for a patient experiencing a ventricular conduction abnormality, such as atrial flutter, is described herein. The female patient, age 40, is admitted to the hospital to initiate treatment. The patient's creatinine clearance is determined to be between >60 mL/min. The patient is connected to an electrocardiograph, and an initial QT interval is determined. Treatment is initiated with an IV loading dose of about 3 µg/kg. The patient's QT interval is measured every 15 minutes during the IV loading dose administration along with HR and BP.

During or following administration of the IV loading dose, the patient's QT interval is determined to be greater than 550 msec. A first maintenance dose is administered to the patient as an oral dose in the reduced amount of 250 The patient's QT interval is monitored following administration of the first oral maintenance dose. The patient's QT interval is still determined to be greater than 550 msec. Subsequent oral maintenance doses of 125 µg are given every 12 to 48 hours or dofetilide administration is discontinued.

Example 11

An example anti-arrhythmic/dofetilide treatment protocol for a patient experiencing a ventricular conduction abnormality, such as atrial flutter, is described herein. The female patient, age 40, is admitted to the hospital to initiate treatment. The patient's creatinine clearance is determined to be between 40 to 60 mL/min. The patient is connected to an electrocardiograph, and an initial QT interval is determined. Treatment is initiated with an IV loading dose of about 1.6 µg/kg. The patient's QT interval is measured every 15 minutes during the IV loading dose administration along with HR and BP.

During and following administration of the IV loading dose, the patient's QT interval is determined to be 550 msec or less and the ΔQTc is not greater than 20% of the patient's initial QTc. A first maintenance dose is administered to the patient as an oral dose of 250 The patient's QT interval is monitored following administration of the first oral maintenance dose. The patient's QT interval is still determined to be less than 550 msec and the ΔQTc is not greater than 20% of the patient's initial QTc. The physician would like to further lengthen the patient's QTc, therefore subsequent oral maintenance doses of 500 µg are given every 12 to 48 hours.

Example 12

An example anti-arrhythmic/dofetilide treatment protocol for a patient experiencing a ventricular conduction abnormality, such as atrial flutter, is described herein. The male patient, age 40, is admitted to the hospital to initiate treatment. The patient's creatinine clearance is determined to be between 20 and 40 mL/min. The patient is connected to an electrocardiograph, and an initial QT interval is determined. Treatment is initiated with an IV loading dose in an amount ranging from 0.1-0.8 µg/kg. The patient's QT interval is measured every 15 minutes during the IV loading dose administration along with HR and BP.

During and following administration of the IV loading dose, the patient's QT interval is not greater than 550 msec and the ΔQTc is not greater than 20% of the patient's initial QTc. A first maintenance dose is administered to the patient as an oral dose of 125 The patient's QT interval is monitored following administration of the first oral maintenance dose and the patient's QT interval is determined to be not greater than 550 msec, and the ΔQTc is not greater than 20% of the patient's initial QTc. A second maintenance dose is administered to the patient as an oral dose of 125 µg and is given 12 to 24 hours after the first maintenance dose. The patient's QTc interval is monitored following administration of the second oral maintenance dose and the patient's QTc interval is determined to be not greater than 550 msec, but the ΔQTc is greater than 20% of the patient's initial QTc (or the patient's QTc interval is determined to be greater than 550 msec, but the ΔQTc is not greater than 20% of the patient's initial QTc, or both are outside of the acceptable range). Subsequent oral maintenance doses of 125 µg are given farther apart and every 24 to 48 hours.

An example anti-arrhythmic/dofetilide treatment protocol for a patient currently being administered oral dofetilide for treatment of a ventricular conduction abnormality, such as atrial flutter, is described herein. The male patient, age 60, is admitted to the hospital to uptitrate dofetilide treatment from a 250 µg BID protocol to a 500 µg BID protocol. The patient's creatinine clearance is determined to be >60 mL/min. The patient is connected to an electrocardiograph, and an initial QTc interval is determined. An IV loading dose is administered to the patient based on an oral target dose of 500 µg, which is administered in an amount of up to 3 µg/kg and is infused over up to 1 hour. The patient's QTc interval is measured every 15 minutes during the IV loading dose administration along with HR and BP.

During and following administration of the loading dose, the patient's QTc interval is determined not to exceed 550 msec and the ΔQTc is not greater than 20% of the patient's initial QTc. A maintenance dose is administered to the patient as an IV dose of up to 3 µg/kg. The IV maintenance dose is administered over a time period of up to 60 minutes. The patient's QTc interval is monitored during and following administration of the IV maintenance dose. The patient's QTc interval still does not exceed 550 msec and the ΔQTc is not greater than 20% of the patient's initial QTc. Subsequent oral maintenance doses of 500 µg are given every 12 hours.

The present disclosure has described particular implementations having various features. In light of the disclosure provided above, it will be apparent to those skilled in the art that various modifications and variations can be made without departing from the scope or spirit of the disclosure. One skilled in the art will recognize that the disclosed features may be used singularly, in any combination, or omitted based on the requirements and specifications of a given application or design. When an implementation refers to "comprising" certain features, it is to be understood that the implementations can alternatively "consist of" or "consist essentially of" any one or more of the features. Other implementations will be apparent to those skilled in the art from consideration of the specification and practice of the disclosure.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the disclosure fall within the scope of the disclosure. Further, all of the references cited in this disclosure including patents, published applications, and non-patent literature are each individually incorporated by reference herein in their entireties and as such are intended to provide an efficient way of supplementing the enabling disclosure as well as provide background detailing the level of ordinary skill in the art.

The invention claimed is:

1. A method, comprising:
   administering 1.5-5.5 µg/kg dofetilide to a patient by way of an intravenous (IV) loading dose over a duration of at least 1 hour and in an amount effective for treating or preventing a cardiovascular condition of the patient;
   wherein the amount of dofetilide in the IV loading dose is in the range of about:
      ±50% of the amount of dofetilide in a target maintenance dose; and
      the target maintenance dose is a 250 µg oral dose of dofetilide.

2. The method of claim 1, wherein the cardiovascular condition is selected from atrial fibrillation, atrial flutter, ventricular tachycardia, hemodynamically stable or unstable ventricular tachycardia, paroxysmal atrial fibrillation, ventricular fibrillation, paroxysmal supraventricular tachycardia, heart failure, coronary artery disease, pulmonary artery hypertension, atrial tachycardia, junctional ectopic tachycardia, or junctional tachycardia.

3. The method of claim 1, further comprising:
   measuring a creatinine clearance of the patient before administering the IV loading dose of dofetilide; and selecting or adjusting the effective amount of the IV loading dose based on the creatinine clearance of the patient.

4. The method of 3, further comprising administering to the patient one or more:
oral dose of dofetilide; or
IV maintenance dose of dofetilide selected from an amount ranging from 0.1-10 µg/kg.

5. The method of claim 4, wherein the patient is NPO and/or unable to take oral dofetilide and is administered the one or more IV maintenance dose of dofetilide.

6. The method of claim 1, wherein the patient has a creatinine clearance in the range of 20-60 mL/min.

7. A method, comprising:
administering an intravenous (IV) loading dose of dofetilide:
to a patient who is currently in normal sinus rhythm;
in an amount effective for treating atrial fibrillation or atrial flutter;
in the range of >3 µg/kg and <12 µg/kg;
over a duration of at least 1 hour; and
administering at least one dose of oral dofetilide to the patient in an amount of 250 µg or 500 µg.

8. A method, comprising:
administering 0.8-3 µg/kg dofetilide to a patient by way of an intravenous (IV) loading dose over a duration of at least 1 hour and in an amount effective for treating or preventing a cardiovascular condition of the patient;
wherein the amount of dofetilide in the IV loading dose is in the range of about:
±50% of the amount of dofetilide in a target maintenance dose; or
the target maintenance dose is a 125 µg oral dose of dofetilide.

9. The method of claim 8, wherein the cardiovascular condition is selected from atrial fibrillation, atrial flutter, ventricular tachycardia, hemodynamically stable or unstable ventricular tachycardia, paroxysmal atrial fibrillation, ventricular fibrillation, paroxysmal supraventricular tachycardia, heart failure, coronary artery disease, pulmonary artery hypertension, atrial tachycardia, junctional ectopic tachycardia, or junctional tachycardia.

10. The method of claim 8, further comprising:
administering to the patient one or more:
oral dose of dofetilide; or
IV maintenance dose of dofetilide in the range of 0.1-10 µg/kg.

11. A method, comprising:
measuring a creatinine clearance of a patient;
selecting an amount of an intravenous (IV) loading dose of dofetilide based on the creatinine clearance of the patient, wherein the amount is effective for treating or preventing a cardiovascular condition of the patient;
administering the IV loading dose of dofetilide to the patient over a duration of at least 1 hour and in an amount that is:
between +5% to +50% of a target maintenance dose; or
between −5% to −50% of the target maintenance dose; and
administering to the patient one or more:
oral dose of dofetilide; or
IV maintenance dose of dofetilide in the range of 0.1-10 µg/kg.

12. The method of claim 11, wherein the cardiovascular condition is selected from atrial fibrillation, atrial flutter, ventricular tachycardia, hemodynamically stable or unstable ventricular tachycardia, paroxysmal atrial fibrillation, ventricular fibrillation, paroxysmal supraventricular tachycardia, heart failure, coronary artery disease, pulmonary artery hypertension, atrial tachycardia, junctional ectopic tachycardia, or junctional tachycardia.

13. The method of claim 11, wherein the patient is NPO and/or unable to take oral dofetilide and is administered the one or more IV maintenance dose of dofetilide.

14. The method of claim 11, wherein the IV loading dose of dofetilide is in an amount of between +5% to +25% of the target maintenance dose.

15. The method of claim 14, further comprising administering the one or more oral dose of dofetilide.

16. The method of claim 11, wherein:
the amount of the IV loading dose is in the range of 1.7-5.5 µg/kg; and
the patient has a creatinine clearance in the range of 40 to 60 mL/min.

17. The method of claim 11, wherein:
the amount of the IV loading dose is in the range of 0.8-2.8 µg/kg; and
the patient has a creatinine clearance in the range of 20 to <40 mL/min.

18. The method of claim 11, wherein:
the amount of the IV loading dose is in the range of 3.5-11 µg/kg; and
the patient has a creatinine clearance of >60 mL/min.

19. The method of claim 18, comprising:
performing ECG monitoring of the patient;
at 2-3 hours after administering the IV loading dose of dofetilide, obtaining a QTc of the patient and determining the QTc of the patient has not increased by greater than 15% from a baseline QTc of the patient or is not greater than 500 msec (550 msec in patients with ventricular conduction abnormalities); and
administering the one or more oral dose of dofetilide to the patient, optionally twice daily, in an amount of:
i. 500 mcg, when the creatinine clearance of the patient is >60 mL/min;
ii. 250 mcg, when the creatinine clearance of the patient is 40 to 60 mL/min; or
iii. 125 mcg, when the creatinine clearance of the patient is 20 to <40 mL/min.

20. The method of claim 18, comprising:
performing ECG monitoring of the patient;
at 2-3 hours after administering the IV loading dose of dofetilide, obtaining a QTc of the patient, and determining the QTc of the patient has increased by greater than 15% from a baseline QTc of the patient or is greater than 500 msec (550 msec in patients with ventricular conduction abnormalities); and
administering the one or more oral dose of dofetilide, in an amount of:
i. 250 mcg, twice daily, for a patient with a creatinine clearance of >60 mL/min;
ii. 125 mcg, twice daily, for a patient with a creatinine clearance of 40 mL/min to 60 mL/min; or
iii. 125 mcg, once daily, for a patient with a creatinine clearance of 20 mL/min to <40 mL/min.

21. The method of claim 18, comprising:
performing ECG monitoring of the patient;
at 2-3 hours after administering the IV loading dose of dofetilide, obtaining a QTc of the patient and determining the QTc of the patient has not increased by greater than 15% from a baseline QTc of the patient or is not greater than 500 msec (550 msec in patients with ventricular conduction abnormalities); and administering the one or more IV maintenance dose of dofetilide to the patient, optionally twice daily, in an amount of:
i. 3.5-11 μg/kg, when the creatinine clearance of the patient is >60 mL/min;
ii. 1.5-6 μg/kg, when the creatinine clearance of the patient is 40 to 60 mL/min; or
iii. 0.8-3 μg/kg, when the creatinine clearance of the patient is 20 to <40 mL/min.

22. The method of claim 18, comprising:
performing ECG monitoring of the patient;
at 2-3 hours after administering the IV loading dose of dofetilide, obtaining a QTc of the patient, and determining the QTc of the patient has increased by greater than 15% from a baseline QTc of the patient or is greater than 500 msec (550 msec in patients with ventricular conduction abnormalities); and
administering one or more IV maintenance dose of dofetilide, in an amount of:
i. 1.5-6 μg/kg, twice daily, for a patient with a creatinine clearance of >60 mL/min;
ii. 0.8-3 μg/kg, twice daily, for a patient with a creatinine clearance of 40 mL/min to 60 mL/min; or
iii. 0.4-3 μg/kg, once or twice daily, for a patient with a creatinine clearance of 20 mL/min to <40 mL/min.

* * * * *